United States Patent [19]

Luly et al.

[11] Patent Number: 5,457,194
[45] Date of Patent: Oct. 10, 1995

[54] SUBSTITUTED ALIPHATIC AMINE-CONTAINING MACROCYCLIC IMMUNOMODULATORS

[75] Inventors: Jay R. Luly; Megumi Kawai, both of Liverty Ville, Ill.

[73] Assignee: Abbott Laboratories, Abbott Park, Ill.

[21] Appl. No.: 99,976

[22] Filed: Jul. 30, 1993

Related U.S. Application Data

[63] Continuation-in-part of Ser. No. 32,958, Mar. 17, 1993, abandoned.

[51] Int. Cl.⁶ .................... C07D 491/18; A61K 31/395
[52] U.S. Cl. .............................. 540/456; 514/291
[58] Field of Search ............................. 540/456

[56] References Cited

U.S. PATENT DOCUMENTS

| | | | |
|---|---|---|---|
| 5,189,042 | 2/1993 | Goulet et al. | 514/291 |
| 5,208,228 | 5/1993 | Ok et al. | 514/183 |
| 5,247,076 | 9/1993 | Goulet et al. | 540/456 |

FOREIGN PATENT DOCUMENTS

| | | | |
|---|---|---|---|
| 428365 | 5/1991 | European Pat. Off. | 514/291 |
| 532089 | 3/1993 | European Pat. Off. | 514/291 |

*Primary Examiner*—Robert T. Bond
*Attorney, Agent, or Firm*—Andreas M. Danckers; Steven R. Crowley

[57] ABSTRACT

Compounds having the formula

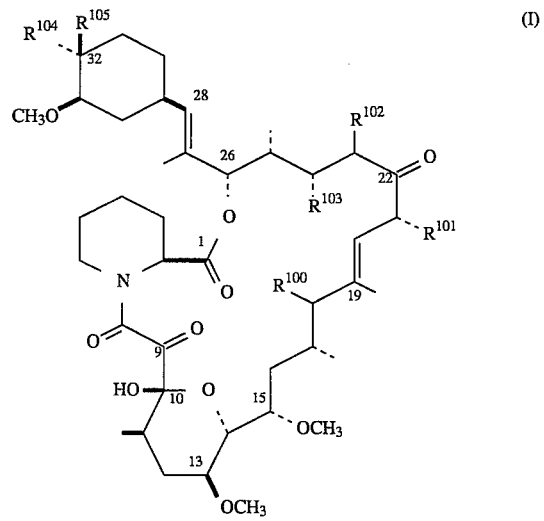

and the pharmaceutically acceptable salts, esters, amides and prodrugs thereof, wherein one of $R^{104}$ and $R^{105}$ is hydrogen, and the other of $R^{104}$ and $R^{105}$ is a radical having the formula

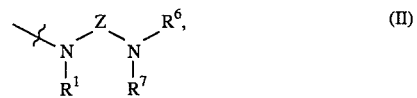

as well as pharmaceutically compositions containing such compounds and methods of immunomodulative therapy utilizing the same.

7 Claims, No Drawings

SUBSTITUTED ALIPHATIC AMINE-CONTAINING MACROCYCLIC IMMUNOMODULATORS

This application is a continuation-in-part of the copending U.S. patent application Ser. No. 08/032,958, filed on Mar. 17, 1993 now abandoned.

FIELD OF THE INVENTION

The present invention relates to novel chemical compounds having immunomodulatory activity, and in particular to macrofide immunosuppressants. More particularly, the invention relates to semisynthetic analogs of ascomycin and FK-506, means for their preparation, pharmaceutical compositions containing such compounds and methods of treatment employing the same.

BACKGROUND OF THE INVENTION

The compound cyclosporine (cyclosporin A) has found wide use since its introduction in the fields of organ transplantation and immunomodulation, and has brought about a significant increase in the success rate for transplantation procedures. Unsatisfactory sideeffects associated with cyclosporine, however, such as nephrotoxicity, have led to a continued search for immunosuppressant compounds having improved efficacy and safety.

Recently, several classes of macrocyclic compounds having potent immunomodulatory activity have been discovered. Okuhara et al., in European Patent Application No. 184162, published Jun. 11, 1986, disclose a number of macrocyclic compounds isolated from the genus Streptomyces. Immunosuppressant FK-506, isolated from a strain of $S.$ $tsukubaensis$, is a 23-membered macrocyclic lactone represented by formula 1a, below. Other related natural products, such as FR-900520 (1 b) and FR-900523 (1 c), which differ from FK-506 in their alkyl substituent at C-21, have been isolated from $S.$ $hygroscopicus$ $yakushimnaensis$. Yet another analog, FR-900525, produced by $S.$ $tsukubaensis$, differs from FK-506 in the replacement of a pipecolic acid moiety with a proline group.

FR-900520, also known as ascomycin, has been previously disclosed by Arai et al. in U.S. Pat. No. 3,244,592, issued Apr. 5, 1966, where the compound is described as an antifungal agent. Monaghan, R. L., et al., on the other hand, describe the use of ascomycin as an immunosuppressant in European Patent Application No. 323865, published Jul. 12, 1989.

Although the immunosuppressive activity of FK-506 has been clinically confirmed, toxicity in mammals has limited its utility. The activity of FK-506 has, however, prompted efforts to discover novel analogs of FK-type compounds which possess superior properties. These efforts include the isolation of new fermentation products, the microbial transformation of existing chemical entities, the chemical modification of these macrocycles, and the synthesis of hybrid species derived from smaller synthetic fragments.

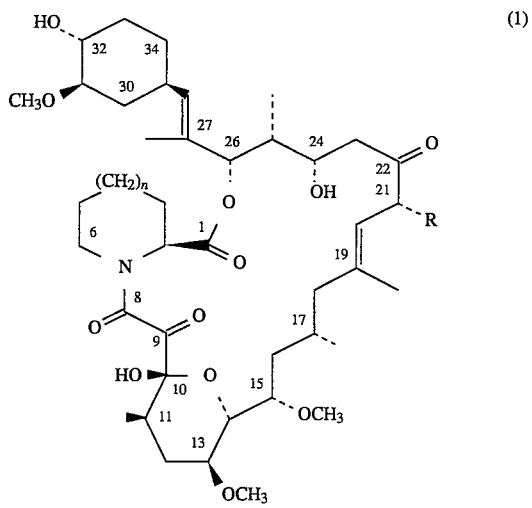

1(a): FK-506 R = $CH_2CH=CH_2$; n = 1

1(b): FR-900520 R = $CH_2CH_3$; n = 1

1(c): FR-900523 R = $CH_3$; n = 1

1(d): FR-900525 R = $CH_2CH=CH_2$; n = 0

Fermentation products of FK-type compounds include C-21-epi derivatives of FK-506; a 31-demethylated derivative of FK-506; 31-oxo-FK-506; and compounds derived from FK-506, FR-900523 and FR-900525 which are characterized by the introduction of hydroxyprotecting groups, formation of a double bond by elimination of water between carbons 23 and 24, oxidation of the hydroxy group at carbon 24 to the ketone, and reduction of the allyl sidechain at carbon 21 via hydrogenation. Other published derivatives include those derived from FK-506 and FR-900520 where the lactone ring is contracted to give a macrocyclic ring containing two fewer carbons.

Several microbial transformations of FK-type compounds at carbon 13 have been published, such as the microbial demethylation of FR-900520 to form the bis-demethylated 13,31-dihydroxy ting-rearranged derivative of FR-900520; the microbial monodemethylation of FK-506 and FR-900520, respectively; and the microbial demethylation of FR-900520 at C-31, as well as a number of other macrocyclic microbial transformation products.

Numerous chemical modifications of the FK-type compounds have been attempted. These include the preparation of small synthetic fragments of FK-type derivatives; a thermal rearrangement of a variety of derivatives of FK-506 which expands the macrocyclic ring by two carbons; and modifications which include methyl ether formation at C-32 and/or C-24, oxidation of C-32 alcohol to the ketone, and epoxide formation at C-9.

Although some of these modified compounds exhibit immunosuppressive activity, the need remains for macrocyclic immunosuppressants which do not have the serious side effects frequently associated with immunosuppressant therapy. Accordingly, one object of the invention is to provide novel semisynthetic macrolides which possess the desired immunomodulatory activity but which may be found to minimize untoward side effects.

Another object of the present invention is to provide synthetic processes for the preparation of such compounds from starting materials obtained by fermentation, as well as chemical intermediates useful in such synthetic processes.

A further object of the invention is to provide pharmaceutical compositions containing, as an active ingredient, one of the above compounds. Yet another object of the invention is to provide a method of treating a variety of disease states, including post-transplant tissue rejection and autoimmune disfunction.

SUMMARY OF THE INVENTION

In one aspect of the present invention are disclosed compounds having the formula

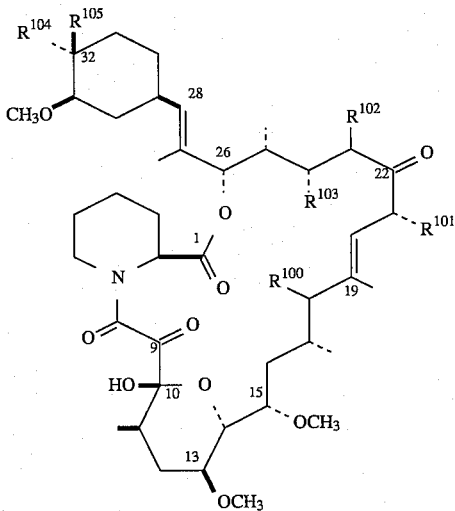

and the pharmaceutically acceptable salts, esters, amides and prodrugs thereof, wherein:

$R^{100}$ is hydrogen, hydroxy, halogen or —$OR^8$;

$R^{101}$ is methyl, ethyl, allyl or propyl;

$R^{102}$ is hydrogen and $R^{103}$ is (a) hydrogen, (b) hydroxy, or (c) hydroxy protected by a hydroxy-protecting group or, taken together, $R^{102}$ and $R^{103}$ form a bond; and one of $R^{104}$ and $R^{105}$ is hydrogen, and the other of $R^{104}$ and $R^{105}$ is a radical having the formula

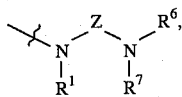

where Z is a divalent radical selected from

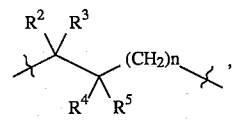

—($C_2$-to-$C_8$ alkylidene)— and —($C_2$-to-$C_4$ alkylidene)-Q-($C_2$-to-$C_4$ alkylidene)— where each such radical may optionally be substituted with one, two or three radicals independently selected from —$OR^8$, —$S(O)_sR^8$, —$S(O)_2NR^8R^{8'}$, —$NR^8R^{8'}$, —$SO_3H$, =$NOR^8$, —$R^{399}$ and —$R^{400}$.

$R^1$, $R^6$ and $R^7$ in the above are independently chosen from (i) hydrogen; (ii) —C(=NH)$NH_2$; (iii) aryl substituted by $R^{301}$, $R^{302}$ and $R^{303}$; (iv) heterocyclic substituted by $R^{301}$, $R^{302}$ and $R^{303}$; and (v) alkyl having j carbon atoms where j is an integer between 1 and 10, inclusive, substituted with between zero and 5 but no more than j radicals selected from —$OR^8$, —$S(O)_sR^8$ where s is an integer between zero and two, inclusive, —$S(O)_2NR^8R^{8'}$, —$NR^8R^{8'}$, —$SO_3H$, =$NOR^8$, —$R^{399}$ and —$R^{400}$.

$R^2$ and $R^3$ in the above are independently chosen from hydrogen, loweralkyl, hydroxyalkyl, —COOH, —COO—(loweralkyl), aminoalkyl, arylalkyl and carboxyalkyl, with the proviso that at least one of $R^2$ and $R^3$ must be other than —COOH or —COO—(loweralkyl). Alternatively, $R^2$ and $R^3$ taken together may be oxo.

$R^4$ and R5 in the above are independently chosen from hydrogen, hydroxy, amino, monoalkylamino, loweralkyl, hydroxyalkyl, —COOH, —COO—(loweralkyl), aminoalkyl, dialkylamino, arylalkyl, or carboxyalkyl, with the two provisos that (i) at least one of $R^4$ and $R^5$ must be other than —COOH or —COO—(loweralkyl), and (ii) at least one of $R^4$ and $R^5$ must be other than hydroxy, amino, monoalkylamino or dialkylamino. Alternatively, $R^4$ and $R^5$ taken together may be oxo.

The number n in the above is an integer between zero and five, inclusive.

The radical $R^{399}$ in the above is (i) hydroxy;

(ii) —C(O)OH;

(iii) —C(O)$OR^8$;

(iv) —($C_3$-to-$C_7$ cycloalkyl);

(v) oxo;

(vi) thiooxo;

(vii) epoxy;

(viii) halogen;

(ix) —CN;

(x) —$N_3$;

(xi) —$NO_2$;

(xii) —$OR^{11'}$;

(xiii) —$OR^{12'}$;

(xiv) —$OR^{12''}$; or (xv) guanidino substituted by hydrogen, loweralkyl, aryl, acyl, arylsulfonyl, alkoxycarbonyl, arylalkoxycarbonyl, aryloxycarbonyl or alkylsulfonyl.

The radical $R^{400}$ in the above is (i) aryl substituted by $R^{301}$, $R^{302}$ and $R^{303}$;

(ii) —Q-aryl where aryl is substituted by $R^{301}$, $R^{302}$ and $R^{303}$;

(iii) heterocyclic substituted by $R^{301}$, $R^{302}$ and $R^{303}$;

(iv) —Q-heterocyclic where heterocyclic is substituted by $R^{301}$, $R^{302}$ and $R^{303}$;

(v) biaryl substituted by $R^{301}$, $R^{302}$ and $R^{303}$;

(vi) —Q-biaryl where biaryl is substituted by $R^{301}$, $R^{302}$ and $R^{303}$;

(vii) —aryl-Q-aryl' where aryl and aryl are the same or different and are independently substituted by $R^{301}$, $R^{302}$ and $R^{303}$;

(viii) —aryl-Q-heterocyclic where heterocyclic and aryl are independently substituted by $R^{301}$, $R^{302}$ and $R^{303}$;

(ix) —heterocyclic-Q-aryl where heterocyclic and aryl are independently substituted by $R^{301}$, $R^{302}$ and $R^{303}$;

(x) —heterocyclic-aryl where heterocyclic and aryl are independently substituted by $R^{301}$, $R^{302}$ and $R^{303}$; and (xi) —aryl-heterocyclic where heterocyclic and aryl are independently substituted by $R^{301}$, $R^{302}$ and $R^{303}$, where the divalent radical —Q— is (i) —($C_1$-to-$C_6$ alkyl)—, (ii) —($C_2$-to-$C_6$ alkenyl)—, (iii) —($C_2$-to-$C_6$ alkynyl)—, (iv) —$(CH_2)_{m''}$O— where m" is between zero and six, inclusive,
(v) —O(CH$_2$)$_{m''}$—,
(vi) —N(R$^8$)C(O)—,
(vii) —C(O)N(R$^8$)—,
(viii) —S(O)$_s$—,
(ix) —N(R$^8$)—,
(x) —N(R$^8$)S(O)$_2$—,
(xi) —S(O)$_2$N(R$^8$)—,
(xii) —C(O)—,
(xiii) —NN—,
(xiv) —CHN—,
(xv) —NCH—,
(xvi) —ONCH—, or
(xvii) —CHNO—.

The radicals R$^8$ and R$^{8'}$ in the above are independently
(i) hydrogen;
(ii) aryl substituted by R$^{301}$, R$^{302}$ and R$^{303}$;
(iii) heterocyclic substituted by R$^{301}$, R$^{302}$ and R$^{303}$;
(iv) —(C$_1$-to-C$_6$ alkyl) substituted by R$^{331}$, R$^{332}$ and R$^{333}$;
(v) —(C$_3$-to-C$_6$ alkenyl) substituted by R$^{331}$, R$^{332}$ and R$^{333}$; and
(vi) —(C$_3$-to-C$_6$ alkynyl) substituted by R$^{331}$, R$^{332}$ and R$^{333}$.

The radicals R$^{331}$, R$^{332}$ and R$^{333}$ in the above are independently
(A) hydrogen,
(A') halogen,
(B) hydroxy,
(C) mono- or dialkylamino,
(D) carboxyl,
(E) carboxamido,
(F) thiol,
(G) alkylthioether,
(H) alkylether,
(I) guanidino,
(J) alkoxycarbonyl,
(K) arylalkoxycarbonyl,
(L) alkoxycarbonylamino,
(M) acylamino,
(N) arylalkoxycarbonylamino,
(O) aryloxycarbonylamino,
(P) acylguanidino,
(Q) arylsulfonylguanidino,
(R) alkoxycarbonylguanidino,
(S) amino,
(T) arylalkoxycarbonylguanidino,
(U) aryloxycarbonylguanidino,
(V) N-alkylcarboxamido,
(X) N,N-dialkylcarboxamido,
(Y) N-arylcarboxamido,
(Z) N,N-diarylcarboxamido,
(AA) —OSO$_2$R$^{11}$,
(BB) oxo,
(CC) epoxy,
(DD) arylether,
(EE) arylthioether,
(FF) arylalkylether,
(GG) arylalkylthioether,
(HH) (heterocyclic)ether,
(II) (heterocyclic)thioether,
(JJ) (heterocylic)alkylether,
(KK) (heterocyclic)alkylthioether,
(LL) aryl,
(MM) heterocyclic,
(NN) —SO$_3$H,
(OO) —S(O)$_2$NR$^{16''}$R$^{16'''}$, or
(PP) —S(O)$_s$R$^{14'}$, where each aryl and heterocyclic moiety is independently substituted by R$^{301}$, R$^{302}$ and R$^{303}$, R$^{11}$ is loweralkyl, arylalkyl substituted by R$^{301}$, R$^{302}$ and R$^{303}$, or aryl substituted by R$^{301}$, R$^{302}$ and R$^{303}$, R$^{14'}$ is hydrogen, loweralkyl, arylalkyl, cycloalkyl or cycloalkylalkyl, and R$^{16'}$ and R$^{16''}$ are independently selected from hydrogen, loweralkyl, hydroxyloweralkyl, carboxyalkyl, thioloweralkyl, thioalkoxyalkyl, guanidinoalkyl, aminoalkyl and arylalkyl.

Alternatively, when appended to a nitrogen atom, R$^8$ and R$^{8'}$ and the nitrogen atom to which they are connected may form a 3- to 7-membered heterocyclic ting which optionally includes up to two additional heteroatoms independently selected from the group consisting of —O—, —S(O)$_s$— and —NRS—.

The radicals R$^{301}$, R$^{302}$ and R$^{303}$ in the above are independently
(i) hydrogen;
(ii) —(C$_1$-to-C$_7$ alkyl);
(iii) —(C$_2$-to-C$_6$ alkenyl);
(iv) halogen;
(v) —(CH$_2$)$_m$NRSR$^{8'}$, where m is an integer between zero and four, inclusive;
(vi) —CN;
(vii) —CHO;
(vii) mono-, di-, tri-, or perhalogenated alkyl;
(ix) —S(O)$_s$R$^8$;
(x) —C(O)NR$^8$R$^{8'}$;
(xi) —(CH$_2$)$_m$OR$^8$;
(xii) —CH(OR$^{12''}$)(OR$^{12'''}$), where R$^{12''}$ and R$^{12'''}$ are independently —(C$_1$-to-C$_3$ alkyl) or, taken together, form an ethylene or propylene bridge;
(xiii) —(CH$_2$)$_m$OC(O)R$^8$;
(xiv) —(CH$_2$)$_m$C(O)OR$^8$;
—OR$^{11'}$, where R$^{11'}$ is selected from the group consisting of
(A) —PO(OH)O-M$^+$,
wherein M$^+$ is a proton or a positively charged inorganic or organic counterion,
(B) —SO$_3$-M$^+$, and
(C) —C(O)(CH$_2$)$_m$C(O)O-M$^+$;
(xvi) —S(O)$_2$NR$^8$R$^{8'}$;
(xvii) —NO$_2$;
(xviii) —N$_3$; or
(xviv) guanidino optionally substituted by a radical selected from the group consisting of loweralkyl, aryl, acyl, arylsulfonyl, alkoxycarbonyl, arylalkoxycarbonyl, aryloxycarbonyl and alkylsulfonyl, subject to the proviso that each of substituents R$^{301}$, R$^{302}$ and R$^{303}$ may comprise no more than twenty non-hydrogen atoms.

Alternatively, taken together, any two adjacent $R^{301}$, $R^{302}$ and $R^{303}$ and the atoms to which they are attached may form a carbocyclic or heterocyclic ring having 5, 6 or 7 ring atoms which optionally includes one or two additional heteroatoms independently selected from the group consisting of —O—, —S(O)$_s$— and —NR$^8$—.

In another aspect of the present invention are disclosed pharmaceutical compositions, comprising a compound of the invention in combination with a pharmaceutically acceptable carder.

In a further aspect of the present invention is disclosed a method for treating a patient in need of immunomodulative therapy, comprising administering to such a patient a therapeutically effective amount of a compound of the invention for such time as is necessary to obtain the desired therapeutic effect.

DETAILED DESCRIPTION OF THE INVENTION

Among the preferred compounds of the present invention are those having formula (I) in which:

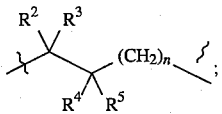

Z is a radical having the formula n is an integer between zero and five, inclusive; and/or $R^1$, $R^6$ and $R^7$ are independently chosen from (i) hydrogen; (ii) —C(=NH)NH$_2$; (iii) aryl substituted by $R^{301}$, $R^{302}$ and $R^{303}$; and (iv) alkyl having j carbon atoms where j is an integer between 1 and 10, inclusive, substituted with between zero and 5 but no more than j radicals selected from —OR$^8$, —S(O)$_2$R$^8$ where s is zero through two, —S(O)$_2$NR$^8$R$^{8'}$, —NR$^8$R$^{8'}$, —SO$_3$H, =NOR$^8$, —R$^{399}$ and —R$^{400}$.

Also preferred are those compounds in which Z is —(C$_2$-to-C$_8$ alkylidene)— where the alkylidene moiety may be substituted with one, two or three radicals independently selected from —OR$^8$, —S(O)$_s$R$^8$, —S(O)$_2$NR$^8$R$^{8'}$, —NR$^8$R$^{8'}$, —SO$_3$H, =NOR$^8$, —R$^{399}$ and —R$^{400}$.

Representative of the compounds of the present invention are those which are demonstrated in Examples 6–43, 47, 54–60 and 62, below, and especially those of Examples 7, 13, 29 and 47. The most preferred of these compounds, and that contemplated as the best mode of the present invention, is the compound described in Example 7.

As used throughout this specification and in the appended claims, the following terms have the meanings specified:

The term "acyl" as used herein refers to an aryl or alkyl group, as defined below, appended to a carbonyl group including, but not limited to, acetyl, pivaloyl, benzoyl and the like.

The term "acylamino" as used herein refers to an aryl or alkyl group, as defined below, appended to a carbonyl group including, but not limited to, acetyl, pivaloyl, benzoyl and the like.

The term "acylguanidino" as used herein refers to an acyl group, as defined above, appended to a nitrogen of a guanidino radical in one of three ways: HN(acyl)C(NH)NH— or H$_2$NC(NH)N(acyl)— or (acyl)NC(NH$_2$)HN—.

The term "alkenyl" as used herein refers to straight or branched chain groups of 2 to 12 carbon atoms containing a carbon-carbon double bond including, but not limited to ethenyl, 1-propenyl, 2-propenyl, 2-methyl-1-propenyl, 1-butenyl, 2-butenyl and the like.

The terms "alkoxy" and "alkylether" as used herein refer to a loweralkyl group, as defined below, attached to the remainder of the molecule through an oxygen atom including, but not limited to, methoxy, ethoxy, isopropoxy, n-butoxy, sec-butoxy, isobutoxy, tert-butoxy and the like.

The term "alkoxycarbonyl" as used herein refers to an alkoxy group, as defined above, attached via a carbonyl group including, but not limited to, methyloxycarbonyl, ethyloxycarbonyl, tert-butyloxycarbonyl, cyclohexyloxycarbonyl and the like.

The term "alkoxycarbonylamino" as used herein refers to an alkoxycarbonyl group, as defined above, appended to an amino group including, but not limited to, methyloxycarbonylamino, tert-butyloxycarbonylamino and the like.

The term "alkoxycarbonylguanidino" as used herein refers to an alkoxycarbonyl group, as defined above, appended to a nitrogen of a guanidino radical in one of three ways: HN(alkoxycarbonyl)C(NH)HN—, H$_2$NC(NH)N(alkoxycarbonyl)— or (alkoxycarbonyl)NC(NH$_2$)HN—.

The term "alkyl" as used herein refers to a monovalent straight chain or branched chain group of 1 to 12 carbon atoms including, but not limited to, methyl, ethyl, n-propyl, isopropyl, n-butyl, sec-butyl, isobutyl, tert-butyl and the like.

The term "N-alkylcarboxamido" as used herein refers to an alkylamino group, as defined above, attached via a carbonyl group and having the formula HN(alkyl)C(O)—.

The term "alkylidene" as used herein refers to a divalent straight or branched chain radical of 2 to 6 crbon atoms including, but not limited to, ethylidine (or -CH$_2$-CH$_2$-), isopropylidine (or —CH(CH$_3$)—CH$_2$—) and the like.

The term "alkylsulfonyl" as used herein refers to an alkyl group, as defined above, attached via a sulfur dioxide diradical including, but not limited to, methanesulfonyl, camphorsulfonyl and the like.

The terms "alkylthioether", "thioalkoxy" and "thiolower-alkoxy" as used herein refer to a loweralkyl group, as previously defined, attached via a sulfur atom including, but not limited to, thiomethoxy, thioethoxy, thioisopropoxy, n-thiobutoxy, sec-thiobutoxy, isothiobutoxy, tert-thiobutoxy and the like.

The term "alkynyl" as used herein refers to straight or branched chain groups of 2 to 12 carbon atoms containing a carbon-carbon triple bond including, but not limited to acetylenyl, propargyl and the like.

The term "amidoalkyl" as used herein refers to a group having the structure —N(R$^{401}$)C(O)R$^{402}$ appended to a loweralkyl group, as previously defined. The groups $R^{401}$ and $R^{402}$ are independently selected from hydrogen, lower alkyl, aryl, arylalkyl, and halosubstituted alkyl. Alternatively, $R^{401}$ and $R^{402}$, taken together, may be —(CH$_2$)$_{aa}$— where aa is an integer of from two to six, inclusive.

The term "aminoalkyl" as used herein refers to a group having the structure —NR$^{403}$R$^{402}$ appended to a loweralkyl group, as previously defined. The groups $R^{403}$ and $R^{404}$ are independently selected from hydrogen, lower alkyl, aryl and arylalkyl. Alternatively, $R^{403}$ and $R^{404}$, taken together, may be —(CH$_2$)$_{bb}$— where bb is an integer of from two to six, inclusive.

The terms "aryl" as used herein refers to carbocyclic aromatic groups including, but not limited to, phenyl, 1- or 2-naphthyl, fluorenyl, (1, 2)-dihydronaphthyl, (1,2,3,4)-tetrahydronaphthyl, indenyl, indanyl and the like.

The terms "arylalkoxy" and "arylalkylether" as used herein refer to an arylalkyl group, as defined below, attached to the parent molecular moiety through an oxygen atom. Arylalkoxy includes, but is not limited to, benzyloxy, 2-phenethyloxy, 1-naphthylmethyloxy and the like.

The term "arylalkoxycarbonyl" as used herein refers to an arylalkoxy group, as defined above, attached via a carbonyl group including, but not limited to, benzyloxycarbonyl, 9-fluorenylmethyloxycarbonyl and the like.

The term "arylalkoxycarbonylamino" as used herein refers to an arylalkoxy group, as defined above, attached via a carbonyl group including, but not limited to, benzyloxycarbonyl, 9-fluorenylmethyloxycarbonyl and the like.

The term "arylaikoxycarbonylguanidino" as used herein refers to an arylaikoxycarbonyl group, as defined above, appended to a nitrogen of a guanidino radical in one of three ways: HN(arylaikoxycarbonyl)C(NH)HN—, H₂NC(NH)N(arylalkoxycarbonyl)— or (arylalkoxycarbonyl)NC(NH₂)HN—.

The term "arylalkyl" as used herein refers to an aryl group, as previously defined, appended to an alkyl group including, but not limited to, benzyl, 1- and 2-naphthylmethyl, halobenzyl, aikoxybenzyl, hydroxybenzyl, aminobenzyl, nitrobenzyl, guanidinobenzyl, fluorenylmethyl, phenylmethyl(benzyl), 1-phenylethyl, 2-phenylethyl, 1-naphthylethyl and the like.

The terms "arylalkylthioether" and "thioarylalkoxy" as used herein refer to an arylalkyl group, as previously defined, attached via a sulfur atom.

The term "N-arylcarboxamido" as used herein refers to an arylamino group, as defined above, attached via a carbonyl group and having the formula HN(aryl)C(O)—.

The terms "arylether" and "aryloxy" as used herein refer to an aryl group, as previously defined, attached to the parent molecular moiety through an oxygen atom. Aryloxy and arylether include, but are not limited to, phenoxy, 1-naphthoxy, 2-naphthoxy and the like.

The term "aryloxycarbonyl" as used herein refers to an aryloxy group, as defined above, attached via a carbonyl group including, but not limited to, phenyloxycarbonyl.

The term "aryloxycarbonylamino" as used herein refers to an aryloxycarbonyl group, as defined above, appended to an amino group including, but not limited to, phenyloxycarbonylamino.

The term "aryloxycarbonylguanidino" as used herein refers to an aryloxycarbonyl group, as defined above, appended to a nitrogen of a guanidino moiety in one of three ways: HN(aryloxycarbonyl)C(NH)HN—, H₂NC(NH)N(aryloxycarbonyl)— or (aryloxycarbonyl)NC(NH₂)HN—.

The term "arylsulfonyl" as used herein refers to an aryl group, as defined above, attached via a sulfur dioxide diradical including, but not limited to p-toluenesulfonyl, benzenesulfonyl and the like.

The term "arylsulfonylguanidino" as used herein refers to an arylsulfonyl group, as defined above, bonded to a nitrogen of a guanidino radical in one of three ways: HN(arylsulfonyl)C(NH)HN— or H₂NC(NH)N(arylsulfonyl)— or (arylsulfonyl)NC(NH₂)HN—.

The terms "arylthioether" and "thioaryloxy" as used herein refer to an aryl group, as defined above, attached via a sulfur atom.

The term "biaryl" as used herein refers to an aryl group, as defined above, appended to an aryl group, wherein the two aryl groups need not be identical including, but not limited to, biphenyl, phenyl-[2-naphthyl]- and the like.

The term "carboxamido" as used herein refers to an amino group attached via a carbonyl group and having the formula —C(O)NH₂.

The term "carboxyalkyl" as used herein refers to a carboxyl group, —CO₂H, appended to a loweralkyl group, as defined below.

The term "cycloalkyl" as used herein refers to a cyclic group of 3 to 8 carbon atoms including, but not limited to, cyclopropyl, cyclobutyl, cyclopentyl, cyclohexyl and the like.

The term "cycloalkylalkyl" as used herein refers to a cycloalkyl group appended to a loweralkyl group as defined below including, but not limited to, cyclohexylmethyl and cyclohexylethyl.

The term "dialkylamino" as used herein refers to a group having the structure —N(loweralkyl)(loweralkyl), where the loweralkyl and loweralkyl' portions are the same or different and are as defined below. Diylkylamino groups include, for example, N,N-methylethylamino, N,N-methylisopropylamino, N,N-ethylisopropylamino and the like.

The term "N,N-dialkylcarboxamido" as used herein refers to an amino group substituted with two alkyl groups, as defined above, wherein the two alkyl groups need not be identical, attached via a carbonyl group and having the formula N(alkyl)(alkyl')C(O)-.

The term "N,N-diarylcarboxamido" as used herein refers to an amino group substituted with two aryl groups, as defined above, wherein the two aryl groups need not be identical, attached via a carbonyl group and having the formula N(aryl)(aryl')C(O)—.

The term "guanidinoalkyl" as used herein refers to a group of the structure —N(R⁴⁰⁵)C(=NR⁴⁰⁶)NHR⁴⁰⁷ appended to a loweralkyl group, as defined below. R⁴⁰⁵, R⁴⁰⁶ and R⁴⁰⁷ are independently selected from hydrogen, loweralkyl, heterocyclic, aminoalkyl and aryl. Alternatively, R⁴⁰⁶ and R⁴⁰⁷, taken together, may be —(CH₂)$_{cc}$— where cc is an integer of from two to six, inclusive.

The terms "halo" and "halogen" as used herein refer to an atom selected from fluorine, chlorine, bromine and iodine.

The term "heterocyclic" as used herein, except where otherwise specified, refers to any aromatic or non-aromatic 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 3 double bonds, (ii) the nitrogen and sulfur heteroatoms as well as the carbon atoms may optionally be oxidized by unsaturation and/or substitution by hydroxy, thiol, oxo or thioxo, (iii) the nitrogen heteroatom may optionally be quatemized, (iv) any of the above heterocyclic rings may be fused to a benzene ring. Representative heterocycles include, but are not limited to, pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrazinyl, piperazinyl, pyrhnidinyl, pyridazinyl, xanthenyl, xanthonyl, xanthopterinyl, oxazoyl, oxazolidinyl, thiouracilyl, isoxazolyl, isoxazolidinyl, morpholinyl, indolyl, quinolinyl, uracilyl, urazolyl, uricyl, thiazolyl, thiazolidinyl, isothiazolyl, isothiazolidinyl, isoquinolinyl, thyminyl, benzimidazolyl, benzothiazolyl, benzoxazolyl, furyl, thienyl and benzothienyl.

The term "(heterocyclic)alkyl" as used herein refers to a heterocyclic group appended to an alkyl group, as previously defined.

The term "(heterocyclic)alkylether" as used herein refers to a (heterocyclic)alkyl moiety, as defined above, attached via an oxygen atom.

The term "(heterocyclic)alkylthioether" as used herein refers to a (heterocyclic)alkyl moiety, as defined above, attached via a sulfur atom.

The term "(heterocyclic)ether" as used herein refers to a heterocyclic moiety, as defined above, attached via an oxygen atom.

The term "(heterocyclic)thioether" as used herein refers to a heterocyclic moiety, as defined above, attached via a sulfur atom.

The terms "hydroxyalkyl" and "hydroxyloweralkyl" as used herein refer to —OH appended to a loweralkyl group, as defined below.

The term "hydroxy-protecting group" as used herein refers to those groups which are known in the art to protect a hydroxy group against undesirable reaction during synthetic procedures and to be selectively removable including, but not limited to, dimethylthexylsilyl, trisubstituted silyl such as tri(lower)alkylsilyl (e.g. tri.methylsilyl, triethylsilyl, tributylsilyl, tri-i-propylsilyl, tert-butyl-dimethylsilyl, tri-tert-butylsilyl, triphenylmethyl-dimethylsilyl, etc.); lower alkyldiarylsilyl (e.g. methyl-diphenylsilyl, ethyl-diphenylsilyl, propyl-diphenylsilyl, tert-butyl-diphenylsilyl, etc.), and the like; triarysilyl (e.g. triphenylsilyl, tri-p-xylylsilyl, etc.); triarylalkylsilyl (e.g. tribenzylsilyl, etc.), acyl substituted with an aromatic group and the like. Other classes of hydroxy-protecting group which may be useful include, but are not limited to, chlorocarbonate analogues such as trimethylsilylethoxycarbonyl, methylthiomethoxyethoxycarbonyl or benzenesulfonylethoxycarbonyl; trimethylsilylethoxymethyl and the like.

The term "loweralkyl" as used herein refers to an alkyl group, as defined above, of 1 to 8 carbon atoms.

The terms "monoalkylamino" and "dialkylamino" refer respectively to one and two alkyl or cycloalkyl groups, as defined above, appended to an amino group including, but not limited to, methylamino, isopropylamino, cyclohexylamino, dimethylamino, N,N-methylisopropylamino; bis-(cyclohexyl)amino and the like.

The term "oxo" as used herein refers to an oxygen atom forming a carbonyl group.

The term "thioalkoxyalkyl" as used herein refers to a thioalkoxy group, as defined above, appended to a loweralkyl group.

The terms "thioalkyl" and "thioloweralkyl" as used herein refer to a loweralkyl group, as defined above, attached via a sulfur atom.

The term "thiooxo" as used herein refers to a sulfur atom forming a thiocarbonyl group.

The term "pharmaceutically acceptable salts, esters, amides and prodrugs" as used herein refers to those carboxylate salts, amino acid addition salts, esters, amides and prodrugs of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non toxic, inorganic and organic acid addition salts of compounds of the present invention. These saks can be prepared in situ during the final isolation and purification of the compounds or by separately teacring the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge, et al., "Pharmaceutical Salts," *J. Pharm. Sci.*, 66:1–19 (1977) which is incorporated herein by reference.)

Examples of pharmaceutically acceptable, non-toxic esters of the compounds of this invention include $C_1$-to-$C_6$ alkyl esters wherein the alkyl group is a straight or branched chain. Acceptable esters also include $C_5$-to-$C_7$ cycloalkyl esters as well as arylalkyl esters such as, but not limited to benzyl. $C_1$-to-$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$-to-$C_6$ alkyl amines and secondary $C_1$-to-$C_6$ dialkyl amines wherein the alkyl groups are straight or branched chain. In the case of secondary amines the amine may also be in the form of a 5 or 6 membered heterocycle containing one nitrogen atom. Amides derived from armnonia, $C_1$-to-$C_3$ aikyl primary amides and $C_1$-to-$C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, "Pro-drugs as Novel Delivery Systems", Vol 14 of the A.C.S. Symposium Series, and in *Bioreversible Carriers in Drug Design*, ed. Edward B. Roche, American Pharmaceutical Association and Pergamon Press, 1987, both of which are incorporated herein by reference. Preferred prodrugs include:

(a) acyloxymethyl esters of carboxylic acids, for example, C(O)-O-CH$_2$-O-C(O)-t-Bu, —C(O)-O-CH(CH$_3$)-O-C(O)—OCH$_2$CH$_3$ or —C(O)—O—Re wherein Re is

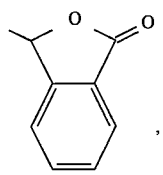

and the like;

(b) (5-methyl-2-oxo-1,3-dioxolen-4-yl)methyl esters of carboxylic acids;

(c) esters derived from alcohol groups in the parent drug by reaction with succinic acid, phosphoric acid, dialkylaminoacetic acid or an amino acid, for example, —O—C(O)—$R^f$ wherein $R^f$ is $(CH_3)_2NCH_2$—, $NH_2CH_2$—, n-PrNHCH$_2$—, $NH_2CH_2CH_2$—, $(CH_3)_2$—, $(CH_3)_2NCH_2CH_2CH_2$—, N-morpholinylmethyl, N-methyl-N'-piperazinylmethyl, phenyl, $CH_3CH_2CH_2$—, $CH_3CH_2CH_2CH_2$— or $HO(O)CCH_2CH_2$—, and the like;

(d) N-Mannich bases of amides or amines, for example, —C(O)—NH—$CH_2R^c$ or —NH—$CH_2R^c$ wherein $R^c$ is piperidin-1-yl, morpholin-1-yl, N-phenylamino, N-phenylpropanolamino, N-methylamino, N-ethylamino, N,N-diethylamino, N,N-dimethylamino, $HO(O)C$—$CH(CH_3)$—NH—, phenyl-NH— or p-$CH_3$-phenyl-NH—, and the like;

(e) N-hydroxymethyl derivatives of amides, for example, —C(O)—NH—$CH_2OH$;

(f) N-acyloxyalkyl derivatives of amides or heterocyclic amines, for example, —C(O)—NH—Rg or =N—Rg wherein Rg is acetoxymethyl, butyryloxymethyl, benzoyloxymethyl, nicotinoyloxymethyl, N,N-dimethylglycyloxymethyl, N,N-diethylglycyloxymethyl, N,N-dipropylglycyloxymethyl, phenylalanyloxymethyl, leucyloxymethyl, phenylglycyloxymethyl or N,N-diethylalanyloxymethyl, and the like;

(g) oxazolidinones derived from ketone groups in the parent drug by reaction with 2-aminoethanol, N-methyl-2-aminoethanol, N-(2-hydroxyethyl)-2-aminoethanol, 2-aminopropanol, 2-amino-2-methylpropanol, 2-amino-2-hydroxymethylpropanol, 3-amino-2-hydroxypropane, 2-amino-1-phenylethanol, 3-aminopropanol or N-methyl-2-amino-1-phenylpropanol, and the like; and (h) enol esters derived from ketone groups in the parent drug, for example, acetyl enol esters, propionyl enol esters, butyryl enol esters, isobutyryl enol esters, pivaloyl enol esters, benzoyl enol esters or N,N-dimethylglycyl enol esters, and the like.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexylcarbodiimede) method, the active ester method (p-nitrophenyl ester method, N-hydroxysuccinic acid imide ester method, cyanomethyl ester method and the like), the Woodward reagent K method, the DCC-HOBT (1-hydroxy-benzotriazole) method and the like. Classical methods for amino acid condensation reactions are described in "Peptide Synthesis" Second Edition, M. Bodansky, Y. S. Klausner and M. A. Ondetti (1976).

As in conventional peptide synthesis, branched chain amino and carboxyl groups at alpha and omega positions in amino acids may be protected and deprotected if necessary. The protecting groups for amino groups which can be used involve, for example, benzyloxycarbonyl (Z), o-chlorobenzyloxycarbonyl ((2-Cl)Z)), p-nitrobenzyloxycarbonyl (Z(NO$_2$)), p-methoxybenzyloxycarbonyl (Z(OMe)), t-amyloxycarbonyl (Aoc), isobornealoxycarbonyl, adamantyloxycarbonyl (Adoc), 2-(4-biphenyl)-2-propyloxy carbonyl (Bpoc), 9-fluorenyl-methoxycarbonyl (Fmoc), methylsulfonylethoxy carbonyl (Msc), trifluoroacetyl, phthalyl, formyl, 2-nitrophenylsulfonyl (Nps), diphenylphosphinothioyl (Ppt) and dimethylphosphino-thioyl (Mpt).

The examples for protecting groups for carboxyl groups involve, for example, benzyl ester (OBzl), cyclohexyl ester, 4-nitrobenzyl ester (OBzlNO$_2$), t-butyl ester (OtBu), 4-pyridylmethyl ester (OPic) and the like.

In the course of the synthesis of certain of the compounds of the present invention, specific amino acids having functional groups other than amino and carboxyl groups in the branched chain such as arginine, cysteine, serine and the like may be protected, if necessary, with suitable protecting groups. It is preferable that, for example, the guanidino group (NG) in arginine may be protected with nitro, p-toluenesulfonyl (Tos), benzyloxycarbonyl (Z), adamantyloxycarbonyl (Adoc), p-methoxybenzenesulfonyl, 4-methoxy-2,6-dimethylbenzenesulfonyl (Mrs) and the like; the thiol group in cysteine may be protected with benzyl, p-methoxybenzyl, triphenylmethyl, acetamidomethyl, ethylcarbamyl, 4-methylbenzyl (4-MeBzl), 2,4,6-trimethylbenzyl (Tmb) and the like; and the hydroxy group in serine may be protected with benzyl (Bzl), t-butyl, acetyl, tetrahydropyranyl (THP) and the like.

Numerous asymmetric centers may exist in the compounds of the present invention. Except where otherwise noted, the present invention contemplates the various stereoisomers and mixtures thereof. Accordingly, whenever a bond is represented by a wavy line, it is intended that both steric orientations are intended.

The compounds of the invention, including but not limited to those specified in the examples, possess immunomodulatory activity in animals. As immunosuppressants, the compounds of the present invention may be useful for the treatment and prevention of immunemediated diseases such as the resistance by transplantation of organs or tissue such as heart, kidney, liver, medulla ossium, skin, cornea, lung, pancreas, intestinum tenue, limb, muscle, nervus, duodenum, small-bowel, pancreatic-islet-cell, etc.; graft-versus-host diseases brought about by medulla ossium transplantation; autoimmune diseases such as rheumatoid arthritis, systemic lupus erythematosus, Hashimoto's thyroidiris, multiple sclerosis, myasthenia gravis, type I diabetes uveitis, allergic encephalomyelitis, glomerulonephritis, and the like; and further infectious diseases caused by pathogenic microorganisms. Further uses may include the treatment and prophylaxis of inflammatory and hyperproliferative skin diseases and cutaneous manifestations of immunologically-mediated illnesses, such as psoriasis, atopical dermatitis, contact dermatitis and further eczematous dermatitises, seborrhoeis dermatitis, Lichen planus, Pemphigus, bullous pemphigoid, Epidermolysis bullosa, urticaria, angioedemas, vasculitides, erythemas, cutaneous eosinophilias, Lupus erythematosus, acne and Alopecia areata; various eye diseases (autoimmune and otherwise) such as keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, Scleritis, Graves' opthalmopathy, Vogt-Koyanagi-Harada syndrome, sarcoidosis, etc.; reversible obstructive airway disease, which includes condition such as asthma (for example, bronchial asthma, allergic asthma, intrinsic asthma, extrinsic asthma and dust asthma), particularly chronic or inveterate asthma (for example, late asthma and airway hyper-responsiveness), bronchitis and the like; inflammation of mucosa and blood vessels such as gastric ulcers, vascular damage caused by ischemic diseases and thrombosis, ischemic bowel diseases, inflammatory bowel diseases, necrotizing enterocolitis, intestinal lesions associated with thenhal burns and leukotriene B$_4$-mediated diseases; intestinal inflammations/allergies such as Coeliac diseases, proctitis, eosinophilic gastroenteritis, mastocytosis, Crohn's disease and ulcerative colitis; food-related allergic diseases which have symptomatic manifestation remote from the gastrointestinal tract (e.g. migraine, rhinitis and eczema); renal diseases such as interstitial nephritis, Goodpasture's syndrome, hemolytic-uremic syndrome and diabetic nephropathy; nervous diseases such as multiple myositis, Guillain-Barre syndrome, Meniere's disease, polyneuritis, multiple neuritis, mononeuritis and radiculopathy; endocrine diseases such as hyperthyroidism and Basedow's disease; hematic diseases such as pure red cell aplasia, aplastic anemia, hypoplastic anemia, idiopathic thrombocytopenic purpura, autoimmune hemolytic anemia, agranulocytosis, pernicious anemia, megaloblastic anemia and. anerythroplasia; bone diseases such as osteoporosis; respiratory diseases such as sarcoidosis, fibroid lung and idiopathic interstitial pneumonia; skin disease such as dermatomyositis, leukoderma vulgaris, ichthyosis vulgaris, photoallergic sensitivity and cutaneous T cell lymphoma; circulatory diseases such as arteriosclerosis, atherosclerosis, aortitis syndrome, polyarteritis nodosa and myocardosis; collagen diseases such as scleroderma, Wegener's granuloma and Sjogren's syndrome; adiposis; eosinophilic fasciitis; periodontal disease such as lesions of gingiva, periodontium, alveolar bone and substantia ossea dentis; nephrotic syndrome such as glomerulonephritis; male pattern aleopecia or alopecia senilis by preventing epilation or providing hair germination and/or promoting hair generation and hair growth; muscular dystrophy; Pyoderma and Sezary's syndrome; Addison's disease; active oxygen-mediated diseases, as for example organ injury such as ischemia-reperfusion injury of organs (such as heart, liver, kidney and digestive tract) which occurs upon preservation, transplantation or ischemic disease (for example, thrombosis and cardiac infraction): intestinal diseases such as endotoxin-shock, pseudomembranous colitis and colitis caused by drug or radiation; renal diseases such as ischemic acute renal insufficiency and chronic renal insufficiency; pulmonary diseases such as toxinosis caused by lung-oxygen or drug (for example, paracort and bleomycins), lung cancer and pulmonary emphysema; ocular diseases such as cataracta, siderosis, retinitis, pigmentosa, senile macular degeneration, vitreal scarfing and corneal alkali bum; dermatitis such as erythema multiforme, linear IgA ballous dermatitis and cement dermatitis; and others such as gingivitis, periodontitis, sepsis, pancreatitis, diseases caused by environmental pollution (for example, air pollution), aging, carcinogenis, metastasis of carcinoma and hypobaropathy; disease caused by histamine or leukotriene-$C_4$ release; Behcet's disease such as intestinal-, vasculo- or neuro-Behcet's disease, and also Behcet's which affects the oral cavity, skin, eye, vulva, articulation, epididymis, lung, kidney and so on. Furthermore, the compounds of the invention are useful for the treatment and prevention of hepatic disease such as immunogenic diseases (for example, chronic autoimmune liver diseases such as the group consisting of autoinunune hepatitis, primary biliary cirrhosis and sclerosing cholangitis), partial liver resection, acute liver necrosis (e.g. necrosis caused by toxin, vital hepatitis, shock or anoxia), B-virus hepatitis, non-A/non-B hepatitis, cirrhosis (such as alcoholic cirrhosis) and hepatic failure such as fulminant hepatic failure, late-onset hepatic failure and "acute-on-chronic" liver failure (acute liver failure on chronic liver diseases), and moreover are useful for various diseases because of their useful activity such as augmentation of chemotherapeutic effect, preventing or treating activity of cytomegalovirus infection, particularly HCMV infection, anti-inflammatory activity, and so on.

Additionally, some compounds appear to possess FK-506 antagonistic properties. The compounds of the present invention may thus be used in the treatment of immunodepression or a disorder involving immunodepression. Examples of disorders involving immunodepression include AIDS, cancer, senile dementia, trauma (including wound healing, surgery and shock) chronic bacterial infection, and certain central nervous system disorders. The immunodepression to be treated may be caused by an overdose of an immunosuppressive macrocyclic compound, for example derivatives of 12-(2-cyclohexyl-1-methylvinyl)13,19,21,27-tetramethyl- 11,28-dioxa-4-azatricyclo[ 22.3.1.0 4,9]octacos-18-ene such as FK-506, or rapamycin. Overdosing of such medicants by patients is quite common upon their realizing that they have forgotten to take their medication at the prescribed time and can lead to serious side effects.

The compounds of the present invention may also find utility in the chemosensitization of drug resistant target cells. Cyclosporin A and FK-506 are known to be effective modulators of P-glycoprotein, a compound which binds to and inhibits the action of anticancer drugs; by inhibiting P-glycoprotein, they are capable of increasing the sensitivity of multidrug resistant (MDR) cells to chemotherapeutic agents. It is believed that the compounds of the invention may likewise be effective at overcoming resistance expressed to clinically useful antitumor drugs such as 5-fluorouracil, cisplatin, methotrexate, vincristine, vinblastine and adriamycin, colchicine and vincristine.

A further situation in which the compounds of the present invention may be used to treat immunosuppression is in vaccination. It is sometimes found that the antigen introduced into the body for the acquisition of immunity from disease acts as an immunosuppressive agent, and so antibodies are not produced by the body and immunity is not acquired. By introducing a compound of the invention into the body (as in a vaccine), the undesired immunosuppression may be overcome and immunity acquired.

Aqueous liquid compositions of the present invention may be particularly useful for the treatment and prevention of various diseases of the eye such as autoimmune diseases (including, for example, conical cornea, keratitis, dysophia epithelialis comeae, leukoma, Mooren's ulcer, sclevitis and Graves' ophthaimopathy) and rejection of corneal transplantation.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat gastrointestinal disorders, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required for to achieve the desired therapeutic effect and to gradually increase the dosage until the desired effect is achieved.

The total daily dose of the compounds of this invention administered to a human or lower animal may range from about 0.001 to about 3 mg/kg/day. For purposes of oral administration, more preferable doses may be in the range of from about 0.005 to about 1.5 mg/kg/day. If desired, the effective daily dose may be divided into multiple doses for purposes of administration; consequently, single dose compositions may contain such amounts or submultiples thereof to make up the daily dose.

The pharmaceutical compositions of the present invention comprise a compound of the invention and a pharmaceutically acceptable carder or excipient, which may be administered orally, rectally, parenterally, intracisternally, intravaginally, intraperitoneally, topically (as by powders, ointments, drops or transdermal patch), bucally, or as an oral or nasal spray. By "pharmaceutically acceptable carder" is meant a non-toxic solid, semi-solid or liquid filer, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like, Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly-(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hardfilled gelatin capsules using such excipients as lactose or milk sugar as well as high molecular weight polyethylene glycols and the like.

The solid dosage forms of tablets, drageel, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formanfide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In nonpressurized powder compositions, the active ingredient in finely divided form may be used in admixture with a larger-sized pharmaceutically acceptable inert carder comprising particles having a size, for example, of up to 100 micrometers in diameter. Suitable inert carders include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquefied gas propellant. The liquefied propellant medium and indeed the total composition is preferably such that the active ingredient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

A further form of topical administration is to the eye, as for the treatment of immunemediated conditions of the eye such as auto immune diseases, allergic or inflammatory conditions, and corneat transplants. The compound of the invention is delivered in a pharmaceutically acceptable ophthalmic vehicle, such that the compotmd is maintained in contact with the ocular surface for a sufficient time period to allow the compound to penetrate the corneal and internal regions of the eye, as for example the anterior chamber, posterior chamber, vitreous body, aqueous humor, vitreous humor, cornea, iris/cilary, lens, choroid/retina and sclera. The pharmaceutically acceptable ophthalmic vehicle may, for example, be an ointment, vegetable oil or an encapsulating material.

Compositions for rectal or vaginal administration are preferably suppositories which can be prepared by mixing the compounds of this invention with suitable non-irritating excipients or catTiers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, Ed., *Methods in Cell Biology*, Volume XIV, Academic Press, New York, N.Y. (1976), p. 33 et seq.

The compounds of the invention may be prepared using one or more of the processes which follow. The starting materials for use in these processes are preferably one of the macrolides isolated from culture media obtained in accordance with known methods by fermentation of microorganisms of the genus *Streptomyces*, which are disclosed in European Patent Application No. 0184162. Samples are available from the Fermentation Research Institute, Tsukuba, Ibaraki 305, Japan under the provisions of the Budapest Treaty, under deposit No. FERM BP-927. This strain has been redeposited on Apr. 27, 1989 with the Agricultural Research Culture Collection International Depository, Peoria, Ill. 61604, USA under the provisions of the Budapest Treaty, under deposit No. NRRL 18488. The macrolide FR-900520 (European Patent Application 0184162), also known as ascomycin, may be prepared in accordance to the published methods of (i) H. Hatanaka, M. Iwami, T. Kino, T. Goto and M. Okuhara, FR-900520 and FR-900523, *Novel immunosuppressants isolated from A streptomyces. I. Taxonomy of the producing strain. J. Antibiot.*, 1988. XLI( 11 ), 1586– 1591; (ii) H. Hatanaka, T. Kino, S. Miyata, N. Inamura, A. Kuroda, T. Goto, H. Tanaka and M. Okuhara, FR-900520 and FR-900523, *Novel immunosuppressants isolated from A streptomyces. H. Fermentation, isolation and physico-chemical and biological characteristics. J. Antibiot.*, 1988. XLI(iii), 1592–1601; (iii) T. Arai, Y. Koyama, T. Suenaga and H. Honda, *Ascomycin, An Antifungal Antibiotic. J. Antibiot.*, 1962. 15(231-2); and (iv) T. Arai in U.S. Pat. No. 3,244,592. One or more of the processes discussed below may be then employed to produce the desired compound of the invention.

Such processes comprise:

(a) producing a compound of formula I, which contains bis(CH—OR) groups, in a corresponding compound wherein R is a protecting group.

(b) producing a compound of formula I, which contains a mono(CH—OR) group, by selective deprotection in a corresponding compound wherein R is a protecting group.

(c) producing a compound of formula I, which contains a CH—OR group, by selective activation of a selected CH—OH group in a corresponding compound wherein —OR is a leaving group which is easily displaced by nucleophilic attack.

(d) producing a compound of formula I, which contains a CH—$R^{100}$ group, by selective displacement of a selected CH—OR group in a corresponding compound wherein —$R^{100}$ is a nucleophile.

(e) producing a compound of formula I, which contains a CH—OH group, by selective and final deprotection in a corresponding compound.

In process (a), suitable protecting groups for hydroxyl include those groups well known in the art such as dimethylthexylsilyl, trisubstituted silyl such as tri(lower)alkylsilyl (e.g. tfimethylsilyl, triethylsilyl, tributylsilyl, tri-i-propylsilyl, tert-butyl-dimethylsilyl, tri-tertbutylsilyl, triphenylmethyl-dimethylsilyl, etc.); lower alkyldia_rylsilyl (e.g. methyldiphenylsilyl, ethyl-diphenylsilyl, propyl-diphenylsilyl, tert-butyl-diphenylsilyl, etc.), and the like; tfiarysilyl (e.g. triphenylsilyl, tri-p-xylylsilyl, etc.); triarylalkylsilyl (e.g. tribenzylsilyl, etc.), and the like, in which the preferred one may be tri($C_1$-to-$C_4$)alkylsilyl and $C_1$-to-$C_4$ alkyldiphenylsilyl, and the most preferred one may be tert-butyldimethylsilyl;

Suitable o-silylations may be carried out using a wide variety of organosilicon reagents such as, but not limited to tert-butyldimethylsilyl chloride, N-(tert-butyldimethylsilyl)-N-methyltrifluoroacetamide (Mawhinney, T., and Madison, M. A. *J. Org. Chem.*, 1982, 47, 3336), tert-butylchlorodiphenylsilane (Hanessian, S. and Lavalice, *P Can. J. Chem.*, 1975, 63, 2975), tert-butyldimethylsilyl tfifluoromethanesulfonate (Mander, L. N. and Sethi, S. P. *Tetrahedron Lett.*, 1984, 25, 5953), dimethylthexylsilyl chloride or dimethylthexylsilyl trifluoromethanesulfonate (Wetter, H. and Oertle, K. *Tetrahedron Lett.*, 1985, 26, 5515), 1-(tert-butyldimethylsilyl)-imidazole and the like.

Carbonate hydroxy-protecting groups may be introduced using a wide variety of a haloformates such as methy, ethyl, 2,2,2-trichloroethyl, isobutyl, vinyl, allyl, 2-(trimethylsilyl)ethyl, 2-(benzenesulfonyl)ethyl, 2-(trimethylsilyl)ethoxy methyl, benzyl and substituted benzyl chloroformates, where benzyl substituents include p-methoxy, 3,4-dimethoxy and p-nitro, in the presence of tertiary base such as pyridine, triethylamine, imidazole, diisopropylethylamine and the like. (*Tetrahedron Lett.*, 1980, 21, 3343; ibid., 1981, 22, 3667; ibid. 1981, 22,969; ibid. 1981, 22, 1933.)

The reaction may be carried out in a solvent which does not adversely affect the reaction (e.g., diethylether, dichloromethane, tetrahydrofuran, chloroform or N,N-dimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, luffdine, picoline, 4-N,N-dimethylaminopyridine, etc.), quinoline, and the like, preferably in the presence of organic bases such as imidazole, triethylamine or pyridine.

The reaction may also be carded out using a starting material having an opposite configuration at a carbon center. In this situation, the following two additional steps are required to yield a starting material having an epimeric hydroxyl moiety: (1) the alcohol is oxidized to its corresponding ketone; and (2) the obtained ketone is reduced under selective conditions. Both chiral centers having either [R]- or [S]-configuration can be obtained selectively and separately.

In process (b), suitable reagents for selective deprotection of a protecting group from C-32 may be carefully carded out using, but not limited to aqueous hydrogen fluoride in acetonitrile (Newton, R. F., Reynolds, D. P., Finch, M. A. W., Kelly, D. R. and Roberts, S. M. *Tetrahedron Lett.*, 1979, 3891), tetraalkyl ammonium fluoride in tetrahydrofuran (Corey, E. J. and Snider, B. B. *J. Am. Chem. Soc.*, 1972, 94, 2549, Corey, E. J. and Venkateswarlu, A. *J. Am. Chem. Soc.*, 1972, 94, 6190) or tetraalkyl ammonium chloridepotassium fluoride in acetonitrile (Carpino, L. A. and Sau, A. C. *J. Chem. Soc., Chem. Commun.* 1979, 514) whererin an alkyl group as defined above, p-toluenesulfonic acid, potassium carbonate in anhydrous methanol (Hurst, D. T. and Malnnes, A. G. *Can. J. Chem.*, 1965, 43, 2004), citric acid in methanol (Bundy, G. L. and Peterson, D.C. *Tetrahedron Lett.*, 1978, 41), acetic acid: water (3:1) (Corey, E. J. and Varma, R. K. *J. Am. Chem. Soc.*, 1971, 93, 7319), Dowex 50W-X8 in methanol (Corey, E. J., Ponder, J. W. and Ulrich, P. *Tetrahedron Lett.*, 1980, 21, 137), boron trifluoride etherate in chloroform (Kelly, D. R., Roberts, M. S. and Newton, R. F. *Synth. Commun.* 1979, 9, 295), methanolic hydrogen fluoride (Hanessian, S. and Lavallee, P. *Can. J. Chem.*, 1975, 53, 2975; ibid., 1977, 55, 562), and pyridinuim fluoride in tetrahydrofuran (Nicolaou, K. C., Seitz, S. P., Pavia, M. R. and Petasis, N. A. *J. Org. Chem.*, 1979, 44, 4011), pyridinium p-toluenesulfonate in ethanol (Prakash, C., Saleh, S. and Blair, I. A. *Tetrahedron Lett.*, 1989, 30, 19), N-bromosuccinimide in dimethylsulfoxide (Batten, R.J. et al., *Synthesis*, 1980, 234), and tetraethyldiboroxane in the presence of catalytic amounts of trimethylsilyl triflate (Dahlhoff, W. V. and Taba, K. M., *Synthesis*, 1986, 561).

The reaction is usually conducted under from cooling to heating, preferably from 0° C. to 50° C. The reaction may require 20 minutes to one day, depending on the reagent and temperature chosen.

In process (c), suitable reagents for activation of an alcohol include acetic anhydride, trifluoromethanesulfonic anhydride (triflic anhydride), fluorosulfonic anhydride, methanesulfonyl chloride (mesyl chloride), p-toluenesulfonyl chloride (tosyl chloride), trifluoroacetic anhydride, trifluoroacetyl chloride, o-nitrobenzenesulfonyl chloride, 1-methyl-2-fluoropyridinium salt and the like.

The activation may be carded out in a solvent which does not adversely affect the reaction (e.g., diethylether, dichloromethane, tetrahydrofuran, chloroform or N,Ndimethylformamide or a mixture thereof). The reaction may require cooling or heating, depending on the activation method chosen. Further, the reaction is preferably conducted in the presence of an organic or inorganic base such as an alkaline earth metal (e.g. calcium, etc.), alkali metal hydride (e.g. sodium hydride, etc.), alkali metal hydroxide (e.g. sodium hydroxide, potassium hydroxide, etc.), alkali metal carbonate (e.g. sodium carbonate, potassium carbonate, etc.), alkali metal hydrogen carbonate (e.g. sodium hydrogen carbonate, potassium hydrogen carbonate, etc.), alkali metal alkoxide (e.g. sodium methoxide, sodium ethoxide, potassium tert-butoxide, etc.), alkali metal alkanoic acid (e.g. sodium acetate, etc.), trialkylamine (e.g. triethylamine, etc.), pyridine compounds (e.g. pyridine, luffdine, picoline, 4-N,N-dimethylaminopyridine, etc.), quinoline, and the like, preferably in the presence of organic bases such as triethylamine or pyridine.

The reaction is usually conducted under from cooling to heating, preferably from −70° C. to 50° C. The reaction may require 20 minutes to one day, depend on the reagent and temperature chosen.

In process (d), a variety of compounds may be prepared from the displacement reactions. An activated hydroxyl group may be reacted with a primary or secondary amine (as defined above and below). The displacement reaction may be carded out in a solvent which does not adversely affect the reaction (e.g. chloroform, dichloromethane, tetrahydrofuran, pyridine, dimethylsulfoxide, N,N-dimethylformamide, hexamethylphosphoramide, etc. or a mixture thereof). The reaction may be conducted above, at, or below ambient temperature, preferably from 0° C. to 50° C. The reaction may require 20 minutes to one week, depend on the reagent chosen.

In process (e), a final deprotection of C-24 protecting group may be carded out according to the method described in process (c).

The compounds, processes and uses of the present invention will be better understood in connection with the following examples, which are intended as an illustration of and not a limitation upon the scope of the invention. Both below and throughout the specification, it is intended that citations to the literature are expressly incorporated by reference. EXAMPLE 1

Formula I: $R_{100}$=H; $R_{101}$=ethyl; $R_{102}$=H;
$R_{103}$=tert-butyldimethylsilyloxy;
$R_{104}$=tert-butyldimethylsilyloxy; $R_{105}$=H.

Ascomycin (25 g, 0.032mol, Formula I: $R_{100}$=H; $R_{101}$=ethyl; $R_{102}$=H; $R_{103}$=OH; $R_{104}$=OH; $R_{105}$=H) was dissolved in a solution of imidazole (43.03 g, 0.64 mol) in dry N,N-dimethylformamide (500 mL) and tert-butyldimethylchlorosilane (47.64 g, 0.32 mol) was added in portions and stirred at room temperature for 24 hours. N,N-dimethylformamide and excess tert-butyldimethylchlorosilane were removed by distillation (bath 35 ° C ) under high vacuum. The solid residue was dissolved in 350 mL of ethylacetate, and the ethyl acetate layer was washed with saturated ammonium chloride aq. solution (200 mL×3), 10%-NaHSO$_4$ (200 mL×3), brine, saturated NaHCO$_3$ (200 mL×3), and brine (200 mL×3). After dried over MgSO$_4$, solvent was removed in vacuo and the solid residue was purified by silica gel chromatography, followed by HPLC eluting with 5% acetone in hexanes providing the title compound (27 g) in 84% yield. MS (FAB) m/z: M+K=1058.

EXAMPLE 2

Formula I: $R_{100}$=H; $R_{101}$=ethyl; $R_{102}$=H;
$R_{103}$=tert-butyldimethylsilyloxy; $R_{104}$=OH: $R_{105}$=H.

To a solution of 48% hydrofluoric acid (3 mL) was added Example 1 (32 g, 0.031 mol) in acetonitrile (500 mL), and the mixture was stirred at room temperature for 90 min. It was cooled to Oo C in an ice bath, and solid NaHCO$_3$ was added to the reaction mixture. It was stirred for 1 hr and solid was removed by filtration. Acetonitrile was removed in vacuo and ethyl acetate (500 mL) was added to the residue, and the organic layer was washed with 10%-NaHCO$_3$ (300 mL×3), brine (250 mL), 10%-NaHSO$_4$ (300 mL×3), and brine (350 mL×3), and dried over anhydrous sodium sulfate. Evaporation of the solvent gave 35 g of crude title compound which was purified by silica gel column chromatography, followed by HPLC eluting with 25%-acetone in hexane. 24.28 g (85 %) of pure compound was obtained. MS (FAB) m/z: M+K=844;

In addition to the title compound, unreacted starting material (Example 1, 1.5 g) and ascomycin (500 mg) were isolated as a pure form.

EXAMPLE 3

Formula I: $R_{100}$=H; $R_{101}$=ethyl; $R_{102}$=H;
$R_{103}$=tert-butyldimethylsilyloxy;
$R_{104}$=O-trifluoromethanesuffonyl; $R_{105}$=H.

The product of Example 2 (4.0 g, 4.42 mmol) was dissolved in 20 mL of methylene chloride at 0° C. Pyridine (3.57 mL, 44.2 mmol), followed by trifluoromethanesuffonic acid anhydride (0.74 mL, 4.42 mmol) were carefully added to the reaction mixture. It was stirred at 0° C. for 20 min and the solvent was removed. Ethyl acetate (50 mL) was added to the residue. The organic layers were washed with brine, saturated NaHCO$_3$ (20 mL×3), brine (20 mL), 10%-NaHSO$_4$ (20 mL×3), brine (20 mL×3) and dried over anhydrous sodium surfate. After the solvent was removed, the title compound was obtained in quantitative yield (4.2 g). This compound was used for the displacement reaction without further purification and characterization.

EXAMPLE 4

Formula I: $R_{100}$=H; $R_{101}$=ethyl; $R_{102}$=H;
$R_{103}$=tert-butyldimethylsilyloxy; $R_{104}$=H; $R^1$=H;
$R^2$H; $R^3$=H; $R^4$=H: $R^5$=H: n=0; $R^6$= and $R^7$ taken together=—(CH$_2$)$_2$—O—(CH$_2$)$_2$13 .

The product of Example 3 (1.97 g, 1.90 mmol) was dissolved in 20 mL of freshly distilled methylene chloride, N-(2-aminoethyl)morpholine (0.70 mL, 7.6 mmol) and triethylamine (1.07 mL, 7.6 mmol) were added, and the reaction was then stirred at room temperature overnight. The reaction mixture was directly poured onto silica gel column and eluted to obtain semi-pure title compound (1.7 mg) in 89% yield. MS (FAB) m/z: M+K=1056. M+H=1017.

EXAMPLE 5

Formula I: $R_{100}$=H; $R_{101}$=ethyl; $R_{102}$=H; $R_{103}$=OH;
$R_{104}$=H; $R^1$=H; $R^2$=H; $R^3$=H; $R^4$=H; $R^5$=H; n=0;
$R^6$=and $R^7$ taken together=—(CH$_2$—O—(CH$_2$)$_2$—.

The product of Example 4 (1.7 g, 1.7 mmol) was dissolved in acetonitrile (10 mL), 48% hydrogen fluoride aqueous solution (48%-HF, 2.0 mL) in acetonitrile (10 mL) was added, and the reaction was then stirred at room temperature for 3 hours. It was cooled to 0° C in an ice bath, and solid NaHCO$_3$ was added to the reaction mixture. It was stirred for 0.5 hr and solid was removed by filtration. Acetonitrile was removed in vacuo and the residue was purified by RP-HPLC, eluting with acetonitrile-water-0.01% trifluoroacetic acid system. Recovered starting material (805 mg) and pure title compound (366 mg) were obtained. MS (FAB) m/z: M+H =904. Deprotection of C-24 protected C-32 adducts such as that obtained in example 4 can be performed under slightly different conditions to give less recovered starting materials: the C-24 protected C-32 adduct (500 mg) is dissolved in acetonitrile (5 mL), 48% hydrogen fluoride aqueous solution (48%-HF, 2.0 mL) in acetonitrile (3 mL) was added, and the reaction is then stirred at room temperature for 2 hours. It is cooled to 0° C. in an ice bath, and solid NaHCO$_3$ is added to the reaction mixture. It is stirred for 0.5 hr and solid is removed by filtration. Acetonirile is removed in vacuo and the residue was purified by RP-HPLC, eluring

EXAMPLE 6

Formula I: $R_{100}$=H; $R_{101}$=ethyl; $R_{102}$=H; $R_{103}$=OH;
$R_{104}$=H; $R^1$=H; $R^2$= H; $R^3$=H; $R^4$=H; $R^5$=H; n=1;
$R^6$=Me; $R^7$=—(CH$_2$)$_3$—NH$_2$.

Following the procedure of Example 4, but replacing N-(2-aminoethyl)morpholine with 3,3'-diamino-N-methyldipropylamine provides the desired C-24 protected C-32 adduct. Deprotection of this material and purification is performed following the procedure of Example 5 to give the titled compound.

EXAMPLE 7

Formula I: $R_{100}$=H; $R_{101}$=ethyl; $R_{102}$=H; $R_{103}$=OH;
$R_{104}$=H; $R^1$=H; $R^2$= H; $R^3$=H; $R^4$=H; $R^5$H; n=1;
$R^6$=Me; $R^7$=Me.

Following the procedure of Example 4, but replacing N-(2-aminoethyl)morpholine with 3-dimethylaminopropylamine provided the desired C-24 protected C-32 adduct. Deprotection of this material and purification was performed following the procedure of Example 5 to give the titled compound. MS (FAB) m/z: M+H=876, M+K=914.

EXAMPLE 8

Formula I: $R_{100}$=H; $R_{101}$=ethyl; $R_{102}$H; $R_{103}$=OH; $R_{104}$=H; $R^1$=H; $R^2$= H; $R^3$=H; $R^4$=H; $R^5$H; n=2; $R^6$=Me; $R^7$=Me.

Following the procedure of Example 4, but replacing N-(2-aminoethyl)morpholine with 4-dimethylaminobutane provides the desired C-24 protected C-32 adduct. Deprotection of this material and purification is performed following the procedure of Example 5 to give the titled compound.

EXAMPLE 9

Formula I: $R_{100}$=H; $R_{101}$=ethyl; $R_{102}$=H; $R_{103}$=OH: $R_{104}$=H; $R^1$=H; $R^2$= H; $R^3$=H; $R^4$=H; $R^5$H; n=1; $R^6$=Bu; $R^7$=Bu.

Following the procedure of Example 4, but replacing N-(2-aminoethyl)morpholine with 3-(di-N-butylamino)-propylamine provides the desired C-24 protected C-32 adduct. Deprotection of this material and purification is performed following the procedure of Example 5 to give the titled compound.

EXAMPLE 10

Formula I: $R_{100}$=H; $R_{101}$=ethyl: $R_{102}$=H; $R_{103}$=OH; $R_{104}$=H; $R^1$=H; $R^2$=H; $R^3$=H; $R^4$=H; $R^5$=OH; n=1; $R^6$=Et; $R^7$=Et.

Following the procedure of Example 4, but replacing N-(2-aminoethyl)morpholine with 1-amino-3-diethylamino-2-propanol provides the desired C-24 protected C-32 adduct. Deprotection of this material and purification is performed following the procedure of Example 5 to give the titled compound.

EXAMPLE 11

Formula I; $R_{100}$=H; $R_{101}$=ethyl: $R_{102}$=H: $R_{103}$=OH; $R_{104}$=H; $R^1$=H; $R^2$=H; $R^3$=H; $R^4$=H; $R^5$=H; n=1; $R^6$=—(CH2)2—OH; $R^7$=—(CH_2)_2—OH.

Following the procedure of Example 4, but replacing N-(2-aminoethyl)morpholine with N,N-bis[(hydroxyethyl)trimethylene]diamine provides the desired C-24 protected C-32 adduct. Deprotection of this material and purification is performed following the procedure of Example to give the titled compound.

EXAMPLE 12

Formula I; $R_{100}$=H; $R_{101}$=ethyl; $R_{102}$=H; $R_{103}$=OH; $R_{104}$=H; $R^1$=H; $R^2$=H; $R^3$=H; $R^4$Me; $R^5$Me; n=1; R6=Me; $R^7$=Me.

Following the procedure of Example 4, but replacing N-(2-aminoethyl)morpholine with N,N,2,2-tetramethyl-1,3-propanediamine provides the desired C-24 protected C-32 adduct. Deprotection of this material and purification is performed following the procedure of Example 5 to give the titled compound.

EXAMPLE 13

Formula I; $R_{100}$=H; $R_{101}$=ethyl: $R_{102}$=H; $R_{103}$=OH; $R_{104}$=H; $R^1$=H; $R^2$=H; $R^3$=H; $R^4$=H; $R^5$=H; n=0; $R^6$=Et; $R^7$=Et.

Following the procedure of Example 4, but replacing N-(2-aminoethyl)morpholine with N,N-diethylethylenediamine provided the desired C-24 protected C-32 adduct. Deprotection of this material and pufificarion was performed following the procedure of Example 5 to give the rifled compound. MS (FAB) m/z: M+H=890, M+K=928. Anal. calc'd. for $C_{49}H_{83}N_3O_{11}$-2 TFA: C, 56.92; H, 7.66; N, 3.75. Found: C, 57.77; H, 7.81; N, 3.81.

EXAMPLE 14

Formula I: $R_{100}$=H; $R_{101}$=ethyl: $R_{102}$=H: $R_{103}$=OH; $R_{104}$=H; $R^1$=H; $R^2$=H; $R^3$=H; $R^4$=H; $R^5$=H; n=0; $R^6$, $R^7$ and the nitrogen to which they are attached=NMe_3Cl.

Following the procedure of Example 4, but replacing N-(2-aminoethyl)morpholine with (2-aminoethyl)trimethylammonium chloride provides the desired C-24 protected C-32 adduct. Deprotecrion of this material and purification is performed following the procedure of Example 5 to give the titled compound.

EXAMPLE 15

Formula I; $R_{100}$=H; $R_{101}$=ethyl: $R_{102}$=H: $R_{103}$=OH; $R_{104}$=H; $R^1$=H; $R^2$=H; $R^3$=H; $R^4$=H; $R^5$=H; n=0; $R^6$=Me; $R^7$=Me.

Following the procedure of Example 4, but replacing N-(2-aminoethyl)morpholine with N,N-dimethylethylenediamine provides the desired C-24 protected C-32 adduct. Deprotection of this material and purificarion is performed following the procedure of Example 5 to give the titled compound.

EXAMPLE 16

Formula I; $R_{100}$=H; $R_{101}$=ethyl; $R_{102}$=H: $R_{103}$=OH; $R_{104}$=H; $R^1$=H; $R^2$=H; $R^3$=H; $R^4$=H; $R^5$=H; n=0; $R^6$=—(CH2)2—OH; $R^7$32 —(CH_2)_2—OH.

Following the procedure of Example 4, but replacing N-(2-aminoethyl)morpholine with N,N-bis(2-hydroxyethyl)ethylenediamine provides the desired C-24 protected C-32 adduct. Deprotection of this material and purification is performed following the procedure of Example 5 to give the titled compound.

EXAMPLE 17

Formula I; $R_{100}$=H; $R_{101}$=ethyl: $R_{102}$=H; $R_{103}$=OH; $R_{104}$=H; $R^1$=H; $R^2$=H; $R^3$=Me; $R^4$=H; $R^5$=H; n=0; $R^6$=Me; $R^7$=Me.

Following the procedure of Example 4, but replacing N-(2-aminoethyl)morpholine with 1-(dimethylamino)-2-propylamine provides the desired C-24 protected C-32 adduct. Deprotection of this material and purification is performed following the procedure of Example 5 to give the titled compound.

EXAMPLE 18

Formula I; $R_{100}$=H; $R_{101}$=ethyl; $H_{102}$=H; $R_{103}$=OH; $R_{104}$=H; $R^1$=H; $R^2$=H; $R^3$H; $R^4$=H: $R^5$=Me; n=0; $R^6$=Me; $R^7$=Me.

Following the procedure of Example 4, but replacing N-(2-aminoethyl)morpholine with N-2,N-2-dimethyl-1,2-propanediamine provides the desired C-24 protected C-32 adduct. Deprotection of this material and purification is performed following the procedure of Example 5 to give the titled compound.

EXAMPLE 19

Formula I; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=iPr; $R^7$=iPr.

Following the procedure of Example 4, but replacing N-(2-aminoethyl)morpholine with N,N-diisopropylethylenediamine provides the desired C-24 protected C-32 adduct. Deprotection of this material and purification is performed following the procedure of Example 5 to give the titled compound.

EXAMPLE 20

Formula I; $R_{100}$=H: $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=—(CH$_2$)$_2$—NH$_2$; $R^7$=—C$_{12}$H$_{25}$.

Following the procedure of Example 4, but replacing N-(2-aminoethyl)morpholine with 4-dodecyldiethylenetriamine provides the desired C-24 protected C-32 adduct. Deprotection of this material and purification is performed following the procedure of Example 5 to give the titled compound.

EXAMPLE 21

Formula I; $R_{100}$=H: $R_{101}$=ethyl; $R_{102}$=H: $R_{103}$=OH; $R_{104}$=H; $R^1$=H; $R^2$=H; $R^3$=H; $R^4$=H; $R^5$=H; n=0; $R^6$=Et, $R^7$=—CH$_2$)$_2$NEt$_2$.

Following the procedure of Example 4, but replacing N-(2-aminoethyl)morpholine with 1,1,4-triethyl diethylenetriamine provides the desired C-24 protected C-32 adduct. Deprotection of this material and purification is performed following the procedure of Example 5 to give the titled compound.

EXAMPLE 22

Formula I; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=Et; $R^7$=—(CH$_2$)$_2$—OH.

Following the procedure of Example 4, but replacing N-(2-aminoethyl)morpholine with N-ethyl-N-beta-hydroxyethylethylenediamine provides the desired C-24 protected C-32 adduct. Deprotection of this material and purification is performed following the procedure of Example 5 to give the titled compound.

EXAMPLE 23

Formula I: $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=Me; $R^7$=Bu.

Following the procedure of Example 4, but replacing N-(2-aminoethyl)morpholine with 2-(methyl-N-butylamino)ethylamine provides the desired C-24 protected C-32 adduct. Deprotection of this material and purification is performed following the procedure of Example 5 to give the titled compound.

EXAMPLE 24a and 24b

Formula I: $R_{100}$=H; $R_{101}$=ethyl; $R_{102}$=H; $R_{103}$=OH; $R_{104}$=H; $R^1$=H; $R^2$=H; $R^3$=CO2H; $R^4$=H; $R^5$=H; n=0; $R^6$=Me; $R^7$=Me and Formula I: $R_{100}$=H; $R_{101}$=ethyl; $R_{102}$=H; $R_{103}$=OH; $R_{104}$=H; $R^1$=H; $R^2$=CO2H; $R^3$=H; $R^4$=H; $R^5$=H; n=0; $R^6$=Me; $R^7$=Me.

Following the procedure of Example 4, but replacing N-(2-aminoethyl)morpholine with dl-4-azaleucine provides the desired Co24 protected C-32 adduct. Deprotection of this material and purification is performed following the procedure of Example 5 to give the titled compounds.

EXAMPLE 25

Formula I; $R_{100}$=H; $R_{101}$=ethyl: $R_{102}$=H; $R_{103}$=OH; $R_{104}$=H; $R^1$=Me; $R^2$=H; $R^3$=H; $R^4$=H; $R^5$=H; n=1; $R^6$=Me; $R^7$=Me.

The product of Example 3 (2.1 g, 2.03 mmol) was dissolved in 10 mL of freshly distilled methylene chloride, N,N,N'-trimethyl-1,3-propanediamine (10.15 mmol) and triethylamine (0.912 mL, 6.09 nunol) were added, and the reaction was then stirred at 50° C for 5 hours and at room temperature for over night. The reaction mixture was directly poured onto silica gel column and eluted to provide the desired C-24 protected C-32 adduct. Deprotection of this compound.

EXAMPLE 26

Formula I: $R_{100}$=H; $R_{101}$=ethyl; $R_{102}$=H; $R_{103}$=OH; $R_{104}$=H; $R^1$= —(CH2)3NMe2; $R^2$=H; $R^3$=H; $R^4$=H: $R^5$=H; n=1; $R^6$=Me; $R^7$Me.

Following the procedure of Example 25, but replacing N,N,N'-trimethyl-1,3-propanediamine with 3,3'-iminobis(N,N-dimethylpropylamine) provides the desired C-24 protected C-32 adduct. Deprotecrion of this material and purification is performed following the procedure of Example 5 to give the rifled compound.

EXAMPLE 27

Formula I: $R_{100}$=H; $R_{101}$=ethyl; $R_{102}$=H; $R_{103}$=OH; $R_{104}$=H; $R^1$=Me; $R^2$=H; $R^3$=H; $R^4$=H; $R^5$=H; n=1; $R^6$=Me; $R^7$=—(CH$_2$)$_3$NHMe.

Following the procedure of Example 25, but replacing N,N,N'-trimethyl-1,3-propanediamine with 3,3'-methyliminobis(N-methylpropylamine) provides the desired C-24 protected C-32 adduct. Deprotection of this material and purification is performed following the procedure of Example 5 to give the rifled compound.

EXAMPLE 28

Formula I: $R_{100}$=H; $R_{101}$=ethyl; $R_{102}$=H; $R_{103}$=OH; $R_{104}$=H; $R^1$=Et; $R^2$=H; $R^3$=H; $R^4$=H; $R^5$=H; n=1; $R^6$=Et; $R^7$=—(CH$_2$)$_3$NHEt.

Following the procedure of Example 25, but replacing N,N,N'-trimethyl-1,3-propanediamine with 7-ethyl-3,7,11-triazatridecane provides the desired C-24 protected C-32 adduct. Deprotection of this material and purification is performed following the procedure of Example 5 to give the titled compound.

EXAMPLE 29

Formula I: $R_{100}$=H; $R_{101}$=ethyl; $R_{102}$=H; $R_{103}$=OH; $R_{104}$=H; $R^1$=Et; $R^2$H; $R^3$=H; $R^4$=H; $R^5$=H; n=0; $R^6$=Et; $R^7$=Et.

Following the procedure of Example 25, but replacing N,N,N'-trimethyl-1,3-propanediamine with N,N,N'-triethylethylenediamine provided the desired C-24 protected C-32 adduct. Deprotection of this material and purification was performed following the procedure of Example 5 to give the rifled compound. MS (FAB) m/z: M+H=918, M+K=956.

EXAMPLE 30

Formula I: $R_{100}$=H; $R_{101}$=ethyl; $R_{102}$=H; $R_{103}$=OH; $R_{104}$=H; $R^1$= —(CH2)2—OH; $R^2$=H; $R^3$=H; $R^4$=H; $R^5$=H; n=0; $R^6$=Et;

Following the procedure of Example 25, but replacing N,N,N'-trimethyl-1,3-propanediamine with 2-(2-diethylaminoethylamine)-ethanol provides the desired C-24 protected C-32 adduct. Deprotection of this material and purification is performed following the procedure of Example 5 to give the titled compound.

EXAMPLE 31

Formula I: $R_{100}$=H; $R_{101}$=ethyl; $R_{102}$=H: $R_{103}$=OH; $R_{104}$=H; $R^1$=Me; $R^2$=H; $R^3$=H; $R^4$ and $R^5$ taken together are O; n=0; $R^6$=Me; $R^7$= —CH$_2$—CO$_2$H.

Following the procedure of Example 25, but replacing N,N,N'-trimethyl- 1,3-propanediamine with sarcosyl-sarcosine and 1 equivalent of N-ethylmorpholine provides the desired C-24 protected C-32 adduct. Deprotection of this material and purification is performed following the procedure of Example 5 to give the rifled compound.

EXAMPLE 32

Formula I; $R_{100}$=H; $R_{101}$=ethyl; $R_{102}$=H; $R_{103}$=OH; $R_{104}$=H; $R^1$=Me; Z=—CH$_2$—C($R^{399}$)—; $R^{399}$=oxo; n=0; $R^6$=Me; $R^7$=Me.

Following the procedure of Example 25, but replacing N,N,N'-trimethyl-1,3-propanediamine with sarcosine dimethylamide provides the desired C-24 protected C-32 adduct. Deprotection of this material and purification is performed following the procedure of Example 5 to give the titled compound.

EXAMPLE 33

Formula I; $R_{100}$=H; $R_{101}$=ethyl; $R_{102}$=H; $R_{103}$=OH; $R_{104}$=H; $R^1$=Me; $R^2$—H; $R^3$—H; $R^4$—H; $R^5$—H; n=0; $R^6$—Me; $R^7$—(CH$_2$)$_2$NHMe.

Following the procedure of Example 25, but replacing N,N,N'-trimethyl-1,3-propanediamine with 1,4,7-trimethyldiethylenetriamine provides the desired C-24 protected C-32 adduct. Deprotection of this material and purification is performed following the procedure of Example 5 to give the titled compound.

EXAMPLE 34

Formula I; $R_{100}$=H: $R_{101}$=ethyl; $R_{102}$=H; $R^{103}$=OH; $R^{104}$=H; $R^1$= —(CH2)2—NEt2; $R^2$=H; $R^3$=H; $R^4$=H; $R^5$=H; n=0; $R^6$=Et; $R^7$=Et.

Following the procedure of Example 25, but replacing N,N,N'-trimethyl-1,3-propanediamine with 1,1,7,7-tetraethyl diethylenetriamine provides the desired C-24 protected C-32 adduct. Deprotection of this material and purification is performed following the procedure of Example 5 to give the titled compound.

EXAMPLE 35

Formula I: $R_{100}$=H; $R_{101}$=ethyl; $R_{102}$=H; $R_{103}$=OH; $R_{104}$=H; $R^1$= —(CH2)2—NMe2; $R^2$=H; $R^3$=H; $R^4$=H; $R^5$=H; n=0; $R^6$=Me; $R^7$=Me.

Following the procedure of Example 25, but replacing N,N,N'-trimethyl-1,3-propanediamine with 1,1,7,7-tetramethyl diethylenetriamine provides the desired C-24 protected C-32 adduct. Deprotecrion of this material and purification is performed following the procedure of Example 5 to give the titled compound.

EXAMPLE 36

Formula I: $R_{100}$=H: $R_{101}$=ethyl; $R_{102}$=H; $R_{103}$=OH; $R_{104}$=H; $R_1$=Et; $R^2$=H; $R^3$=H; $R^4$=H; $R^5$=H; n=0; $R^6$=Et; $R^7$= —(CH$_2$)$_2$NEt(CH$_2$)$_2$NHEt.

Following the procedure of Example 25, but replacing N,N,N'-trimethyl-1,3-propanediamine with 1,4,7,10-tetraethyltfiethylenetetramine provides the desired C-24 protected C-32 adduct. Deprotection of this material and purification is performed following the procedure of Example 5 to give the titled compound.

EXAMPLE 37

Formula I: $R_{100}$=H; $R_{101}$=ethyl; $R_{102}$=H; $R_{103}$=OH; $R^4$=H; $R^1$=H; $R^2$=H; $R^3$=H; $R^4$=H; $R^5$=H; n=0; $R^6$=H; $R^7$=—(CH$_2$)$_2$NMe$_2$.

Following the procedure of Example 4, but replacing N-(2-aminoethyl)morpholine with N(dimethylaminoethyl)ethylenediamine provides the desired C-24 protected C-32 adduct. Deprotection of this material and purification is performed following the procedure of Example 5 to give the titled compound.

EXAMPLE 38

Formula I; $R_{100}$=H: $R_{101}$=ethyl; $R_{102}$=H: $R_{103}$=OH; $R_{104}$=H; $R^1$= —(CH2)2—NH$_2$; $R^2$=H: $R^3$=H; $R^4$=H; $R^5$=H; n=0; $R^6$=Me; $R^7$=Me.

Following the procedure of Example 25, but replacing N,N,N'-trimethyl-1,3-propanediamine with N-Boc-N'-(dimethylaminoethyl)-ethylenediamine provided the desired Boc-amino protected and C-24 protected C-32 adduct. Deprotection of this material and purification is performed following the procedure of Example 5 to give the rifled compound.

EXAMPLE 39

Formula I: $R_{100}$=H; $R_{101}$=ethyl; $R_{102}$=H; $R_{103}$=OH; $R_{104}$=H; $R^1$=H; $R^2$=—$CO_2$tBu; $R^3$=H; $R^4$=H; $R^5$=H; n=3; $R^6$=Boc; $R^7$=H.

Following the procedure of Example 4, but replacing N-(2-aminoethyl)morpholine with epsilon-Boc-L-Lys-OtBu provides the desired C-24 protected C-32 adduct. Deprotection of this material is performed using Bu$_4$NF followed by purification by reverse phase HPLC to give the titled compound.

Formula I: $R_{100}$=H; $R_{101}$=ethyl; $R_{102}$=H; $R_{103}$=OH; $R_{104}$=H; $R^1$=H; $R^2$=—$CO_2$tBu; $R^3$=H; $R^4$=H; $R^5$=H; n=3; $R^6$=Boc; $R^7$=H.

The resultant compound of example 39 is treated with TFA in dichloromethane, and purification is performed of this material is achieved by reverse phase HPLC to give the titled compound.

EXAMPLE 41

Formula I: $R_{100}$=H; $R_{101}$=ethyl; $R_{102}$=H: $R_{103}$=OH; $R_{104}$=H; $R^1$=H; $R^2$=—CO2H; $R^3$=H; $R^4$=H; $R^5$=H; n=3; $R^6$=H; $R^7$= —C(=NH)NH$_2$.

The amidination of the resultant compound of example 40 is carried out according to literature methods (Salvadori, S.; Sarto, G. P.; Tomatis, R; Eur. J. Med. Chem. Chim. Ther. 18:489 (1983)) to give the titled compound.

EXAMPLE 42

Formula I: $R_{100}$=H; $R_{101}$=ethyl: $R_{102}$=H; $R_{103}$=OH; $R_{104}$=H; $R^1$=H; $R^2$=H; $R^3$=—CO2H; $R^4$=H; $R^5$=H; n=3; $R^6$=H; $R^7$=H.

Following the procedures of Examples 39 and 40, but replacing epsilon-Boc-L-Lys-OtBu with epsilon-Boc-D-Lys-OtBu provided the titled compound.

EXAMPLE 43

Formula I: $R_{100}$=H; $R_{101}$=alkyl; $R_{102}$=H; $R_{103}$=OH; $R_{104}$=H; R1=H; $R^2$=H; $R^3$=H; $R^4$=H; $R^5$=H; n=1; $R^6$=Me; $R^7$=Me.

Following the procedure of Example 7, but replacing ascomycin (Formula I: $R_{100}$=H; $R_{101}$= ethyl; $R_{102}$=H; $R_{103}$=OH; $R_{104}$=OH; $R_{105}$=H) with FK-506 (Formula I: $R_{100}$=H; $R_{101}$=allyl; $R_{102}$=H; $R_{103}$ =OH; $R_{104}$=OH; $R_{105}$=H) provides the titled compound.

EXAMPLE 44

Formula I: $R_{100}$=H; $R_{101}$=ethyl: $R_{102}$=H: $R_{103}$=OH; $R_{104}$ and $R_{105}$ taken together form an oxo group.

Methylsulfide-chlorine complex was prepared by adding oxalyl chloride (0.32 g) into a stirred solution of dimethylsulfoxide (0.44 g) in methylene chloride (4 mL) and stirring at –70° C for 0.5 hours. The solution of the complex was added in slow dropwise fashion into a stirring solution of ascomycin (1.6 g) in methylene chloride (5 mL) at –70° C. After stirring for 0.25 hours, triethylamine (1.4 g) was added at –70° C. Stirring was continued at –70° C. for 0.5 hours and then at room temperature for 1 hour. The reaction mixture was then diluted with ether (100 mL), washed with 1 N HCl (aq) (2×30 mL), saturated brine (30 mL), dried over magnesium sulfate and solvent removed. The product was purified on silica gel (70 g) with ether elution. Yield: 0.95 g; MS (FAB) m/z: M+H =790.

EXAMPLE 45

Formula I: $R_{100}$=H; $R_{101}$=ethyl; $R_{102}$=H; $R_{103}$=OH; $R_{104}$=H; $R_{105}$=OH.

Lithium tri-t-butoxyaluminum hydride(0.2 mL, 1 M in THF) was added slowly into a stirred solution of the product of Example 44 (0.056 g) in dry THF (1 mL) at –70° C. under nitrogen. After stirring at –70° C for 3 hours, it was partitioned between ether (50 mL) and 1 N HCl (10 mL). The organic phase was dried over magnesium sulfate, the solvent was removed and the product purified by prep TLC (35% acetone in hexanes). Yield: 0.025 g; MS (FAB) m/z: M+K =830.

EXAMPLE 46

Formula I: $R_{100}$=H; $R_{101}$=ethyl; $R_{102}$=H: $R_{103}$=OH: $R_{104}$=H; $R_{105}$= O-trifluoromethanesulfonyl.

The product of Example 45 (4.0 g, 4.42 mmol) is dissolved in 20 mL of methylene chloride at 0° C. pyridine (3.57 mL, 44.2 mmol), followed by trifluoromethanesulfonic acid anhydride (0.74 mL, 4.42 mmol) are carefully added to the reaction mixture. It is stirred at 0° C. for 20 minutes and the solvent is removed. Ethyl acetate (50 mL) is added to the residue. The organic layers are washed with brine, saturated NaHCO$_3$ (20 mL×3), brine (20 mL), 10%-NaHSO$_4$ (20 mL×3), brine (20 mL×3) and dried over anhydrous sodium sulfate. After the solvent is removed, the title compound is obtained. This compound is used for the displacement reaction without further purification and characterization.

EXAMPLE 47

Formula I: $R_{100}$=H; $R_{101}$=ethyl; $R_{102}$=H; $R_{103}$=OH; $R_{105}$=H; $R^1$=H; $R^2$=H; $R^3$=H; $R^4$=H; $R^5$=H; n=1; $R^6$=Me; $R^7$=Me.

The product of Example 46 (2.03 mmol) is dissolved in 10 mL of freshly distilled methylene chloride, dimethylaminopropylamine (10.15 mmol) and triethylamine (6.09 mmol) are added, and the reaction was then stirred at room temperature overnight. The reaction mixture was directly poured onto silica gel column and eluted to obtain pure title compound. MS (FAB) m/z: M+H=876, M+K=914.

EXAMPLE 48

Formula I: $R_{100}$=H; $R_{101}$=ethyl; $R_{102}$ and $R_{103}$ taken together form a bond; $R_{104}$=OH; $R_{105}$=H.

Ascomycin (10 g, 12.6 mmol) and pyridinium p-toluene sulfonate (1 g, 3.98 mmol) were dissolved in 200 mL of toluene and stirred at 70° C. over night. Solvent was removed, and the residue was purified by silica gel column chromatography, eluting with 5–10% acetone in hexane. The title compound (8.89 g) was isolated in 91% yield. MS (FAB) m/z: M+K=812.

EXAMPLE 49

Formula I: $R_{100}$=H; $R_{101}$=ethyl; $R_{102}$=H; $R_{103}$=H; $R_{104}$=OH; $R_{105}$=H.

The product of Example 48 (2.2 g, 2.8 mmol) was hydrogenated in the presence of 5% rhodium on alumina (220 mg) in 100 mL of ethanol at room temperature for 1 hour. After filtered, the filtrate was concdntrated in vacuo to obtain the title compound in quantitative yield. The obtained product was then loaded on silica gel column, and eluted with 5–10% acetone in hexane to obtain the pure title compound in 75–80 yield. MS (FAB) m/z: M+K=814.

EXAMPLE 50

Formula I: $R_{100}$=H; $R_{101}$=n-propyl; $R_{102}$=H; $R_{103}$=OH; $R_{104}$=OH; $R_{105}$=H.

FK-506 (150 mg, 0.2 mmol) was dissolved in 6 mL of ethyl acetate and 30 mg of 10%-palladium on charcoal was added. It was hydrogenated at room temperature for 20 minutes under one atmosphere pressure. After filtration of the catalyst, the solvent was evaporated to dryness to yield 150 mg of crude product, which was then purified by silica gel column chromatography, eluting with a chloroform:acetone (5:1) mixture. The pure rifled compound (114 mg) was isolated in 76% yield. MS (FAB) m/z: M+K=844.

EXAMPLE 51

Formula I: $R_{100}$=H; $R_{101}$=ethyl; $R_{102}$ and $R_{103}$ taken together form a bond; $R_{104}$=O-trifiuoromethanesulfonyl; $R_{105}$=H.

Following the procedure of Example 3, but replacing the resultant compound of Example 2 with the resultant compound of Example 48 gives the titled compound.

EXAMPLE 52

Formula I: $R_{101}$=H; $R_{101}$=ethyl; $R_{102}$=H; $R_{103}$=H; $R_{104}$= O-trifluoromethanesulfonyl;

Following the procedure of Example 3, but replacing the resultant compound of Example 2 with the resultant compound of Example 49 gives the titled compound.

EXAMPLE 53

Formula I: $R_{100}$=H; $R_{101}$=n-propyl; $R_{102}$=H; $R_{103}$=OH; $R_{104}$= O-trifluoromethanesulfonyl; $R_{105}$=H.

Following the procedures of Examples 1–3, but replacing ascomycin with the resultant compound of Example 50, the rifled compound is obtained.

EXAMPLE 54

Formula I: $R_{100}$=H;. $R_{101}$=ethyl; $R_{102}$ and $R_{103}$ taken together form a bond; $R_{104}$=H; $R^1$32 H; $R^2$=H; $R^3$=H; $R^4$=H; $R^5$H; n=1; $R^6$=Me; $R^7$=Me.

The product of Example 51 (2.03 mmol) is dissolved in 10 mL of freshly distilled methylene chloride, dhnethylaminopropylamine (10.15 minol) and Methylamine (6.09 retool) are added, and the reaction is then stirred at room temperature overnight. The reaction mixture is directly poured onto silica gel column and eluted to obtain pure title compound.

EXAMPLE 55

Formula I: $R_{100}$=H; $R_{101}$=ethyl; $R_{102}$=H; $R_{103}$=H; $R_{104}$=H; $R^1$=H; $R^2$= H; $R^3$=H: $R^4$=H; $R^5$=H; n=1; $R^6$=Me: $R^7$=Me.

The product of Example 52 (2.03 mmol) is dissolved in 10 mL of freshly distilled methylene chloride, dimethylaminopropylamine (10.15 mmol) and triethylamine (6.09 mmol) are added, and the reaction is then stirred at room temperature overnight. The reaction mixture is directly poured onto silica gel column and eluted to obtain pure title compound.

EXAMPLE 56

Formula I: $R_{100}$=H: $R_{101}$=propyl; $R_{102}$=H; $R_{103}$=OH; $R_{104}$=H; $R^1$=H; $R^2$=H: $R^3$=H; $R^4$=H; $R^5$=H; n=1; $R^6$=Me; $R^7$=Me.

Following the procedure of Example 7, but replacing ascomycin (Formula I: $R_{100}$=H: $R_{101}$= ethyl; $R_{102}$=H; $R_{103}$=OH; $R_{104}$=OH; $R_{105}$=H) with the resultant compound of Example 53 provides the titled compound.

EXAMPLE 57

Formula I: $R_{100}$=H: $R_{101}$=methyl; $R_{102}$=H: $R_{103}$=OH; $R_{104}$=H; $R^1$=H; $R^2$=H; $R^3$=H; $R^4$=H; $R^5$=H; n=1; $R^6$=Me; $R^7$=Me.

Following the procedure of Example 7, but replacing ascomycin (Formula I: $R_{100}$=H: $R_{101}$= ethyl; $R_{102}$=H; $R_{103}$=OH; $R_{104}$=OH; $R_{105}$=H) with FK-523 (Fonnula I: $R_{100}$=H; $R_{101}$=methyl; $R_{102}$=H; $R_{103}$=OH; $R_{104}$=OH; $R_{105}$=H) provides the titled compound.

EXAMPLE 58

Formula I: $R_{100}$=OH; $R_{101}$=ethyl; $R_{102}$=H: $R_{103}$=H; $R_{104}$=H; $R^1$=H; $R^2$=H; $R^3$=H; $R^4$=H; $R^5$=H; n=1; $R^6$=Me; $R^7$=Me.

The product of Example 55 (5 mmol) is dissolved in 25 mL of methylene chloride. This is added to a solution of 5 mL of methylene chloride containing tert-butyl hydroperoxide in 2,2,4trimethylpentane (6.65 mL, 20 mmol) and selenium oxide (830 mg, 7.5 mmol). The reaction is monitored by thin layer chromatography. The mixture is stirred at room temperature until the starting material is disappeared. Solvents are removed and an approximately 100 mL of ethyl acetate is added to the residue. The ethyl acetate layer is washed with brine, dried over anhydrous sodium sulfate. Purification of the title compound is carded out by high performance liquid chromatography.

EXAMPLE 59

Formula I; $R_{100}$=F: $R_{101}$=ethyl; $R_{102}$=H; $R_{103}$=H: $R_{104}$=H; $R^1$=H; $R^2$=H; $R^3$=H; $R^4$=H; $R^5$=H; n=1; $R^6$=Me; $R^7$=Me.

A solution of the product of example 58 (100 mg) in 1 mL of methylene chloride is cooled to −78° C. in a dry ice/isopropanol bath. To this stirred solution, diethylmninosulfur trifluoride (10 mL) is added. After 3 minutes, saturated sodium bicarbonate (lmL) is added followed by 5 mL of ethyl acetate and the mixture is warmed to room temperature. Extraction from ethyl acetate, drying over anhydrous magnesium sulfate and purification by high performance liquid chromatography gives the pure title compound.

EXAMPLE 60

Formula I: $R_{100}$=OC(O)CH$_3$; $R_{101}$=ethyl; $R_{102}$=H; $R_{103}$=H; $R_{104}$=H; $R^1$=H; $R^2$=H; $R^3$H; $R^4$=H: $R^5$=H; n=1; $R^6$=Me; $R^7$=Me.

A solution of the product of example 58 (100 mg) in 1 mL of pyridine is cooled to 0° C. in an ice bath. To this stirred solution, N,N-dimethylaminopyridine (3 mg), followed by acetic acid anhydride (20 ml) are added. After stirred at 0° C. for 5 hours, it is stirred at room temperature for one overnight. Extraction from ethyl acetate, drying over anhydrous magnesium sulfate and purification by high performance liquid chromatography gives the pure title compound.

EXAMPLE 61

Formula I: $R_{100}$=H; $R_{101}$=ethyl; $R_{102}$=H; $R_{103}$=tert-butyldimethylsilyloxy; $R_{104}$=O-fluorosulfonyl; $R_{105}$=H.

To a stirred solution of the product of Example 2 (0.5 g, 0.6 mmol) in CH$_2$Cl$_2$ (5 mL) at −70° C. was added 2,6-lutidine (0.26 mL, 2.2 mmol), followed by fluorosulfonyl anhydride (0.12 mL, 1.1 mmol). The reaction mixture was warmed to 0° C., and stirred for 0.5 hr. The reaction was partitioned between ether, ice cold 0.1 N HCl and brine. The organic layer was dried over Na2SO4, filtered and evaporated to give 0.53 g of the crude tittle compound in 97% yield. FAB-MS (m/z) 1026 (M+K)

EXAMPLE 62

Formula I: $R_{100}$=H; $R_{101}$=ethyl; $R_{102}$=H; $R_{103}$=OH; $R_{104}$=H; $R^1$=H; $R^2$=H: $R^3$=H; $R^4$=H; $R^5$=H; n=1; $R^6$=Me; $R^7$=Me.

To a stirred solution of the product of Example 61 (0.20 g, 0.2 rmnol) in CH3CN (1.5 mL) at 0° C. is added 3-dimethylaminopropylamine (0.4 mmol). The reaction is stirred at room temperature overnight. The product is isolated by RP-HPLC (41.4 mm ID, Dynamax-60A, C18 column) to obtain the C-24 protected product. To a stirred solution of the above product (0.1 mmol) in CH$_3$CN (2 mL) is added 48% aqueous HF (0.4 mL) in CH$_3$CN (1 mL). After stirring at room temperature for 1.5 hr, the product is purified by RP-HPLC to give the rifled compound.

EXAMPLE 63

In Vitro Assay of Biological Activity

The immunosuppressant activity of the compounds of the present invention was deternfined using the human mixed lymphocyte reaction (MLR) assay described by Kino, T. et al. in *Transplantation Proceedings* XIX(5):36–39, Suppl. 6 (1987), incorporated herein by reference. The results of the assay, shown below in Table 1, demonstrate that the compounds tested are effective immunomodulators at sub-micromolar concentrations.

TABLE 1

| Ex. # | IC$_{50}$ (M) |
| --- | --- |
| 7 | <1 × 10$^{-6}$ |
| 13 | <1 × 10$^{-6}$ |
| 29 | <1 × 10$^{-6}$ |
| 47 | <1 × 10$^{-6}$ |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

What is claimed is:

1. A compound having the formula

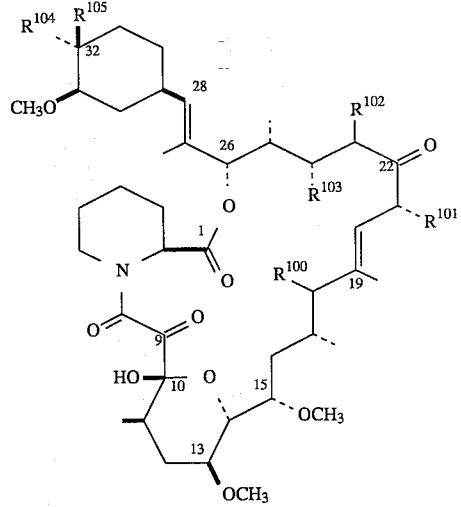

is selected from C$_1$-to-C$_6$ alkyl esters, C$_5$-to-C$_7$ cycloalicyl esters and or a pharmaceutically acceptable salt, ester, amide or prodrug thereof wherein the ester arylalkyl esters and wherein the amide results from reaction of a carboxylic acid moiety in the compound of formula I with NH$_3$, NH$_2$(C$_1$-to-C$_6$ alkyl), NH(C$_1$-to-C$_6$ alkyl)$_2$ or a 5- or 6-membered heterocycle containing one nitrogen atom and wherein the prodrug is selected from the group consisting of (a) acyloxymethyl esters of Carboxylic acids, (b)(5-methyl-2-oxo-1,3-dioxolen-4-yl)methyl esters of carboxylic acids, (c) esters derived from alcohol groups in the .parent druq by reaction with succinic acid, phosphoric acid, dialkylaminoacetic acid or an amino acid (d) N-Mannich bases of amides or amines, (e) N-hydroxymethyl derivatives of amides, (f) N-acyloxyalkyl derivatives of amides or heterocyclic amines, oxazolidinones derived from ketone groups in the parent drug by reaction with 2-aminoethanol, N-methyl-2-aminoethanol, N—(Z-hydroxyethyl)-2-aminoethanol, 2-aminopropanol, 2-amino-2-methylpropanol, 2-amino-2hydroxymethylpropanol, 3-amino-Z-hydroxypropane, 2-amino-1-phenylethanol, 3-aminopropanol or N-methyl-2-amino-1-phenylpropanol and (h) enol esters derived from ketone groups in the parent drug, wherein $R_{100}$ is selected from the group consisting of hydrogen, hydroxy, halogen and —$OR^8$ wherein $R^8$ is defined as herein;

$R^{101}$ is selected from the group consisting of methyl, ethyl, allyl and propyl;

$R^{102}$ is hydrogen and $R^{103}$ is selected from the group consisting of (a) hydrogen, (b) hydroxy, and (c) hydroxy protected by a hydroxy-protecting group selected from dimethylthexylsilyl, tri($C_1$-to-$C_8$-alkyl)silyl, $C_1$-to-$C_{12}$-alkyldiarylsilyl, triarylsilyl, tri(aryl-$C_1$-to-$C_{12}$-alkyl)silyl trimethylsilylethoxycarbonyl, methylthiomethoxyethoxycarbonyl. benzenesulfonylethoxycarbonyl and trimethylsilylethoxymethyl or, taken together, $R^{102}$ and $R^{103}$ form a bond; and one of $R^{104}$ and $R^{105}$ is hydrogen, and the other of $R^{104}$ and $R^{105}$ is a radical having the formula

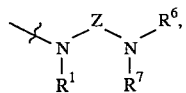

where Z is a divalent radical selected from the group consisting of

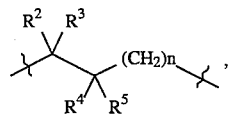

—($C_2$-to-$C_8$alkylidene)— and —($C_2$-to-$C_4$alkylidene)-Q—($C_2$-to-$C_4$alkylidene)— where each such radical is optionally substituted with between one and three radicals independently selected from the group consisting of —$OR^8$, —$S(O)_sR^8$, —$S(O)_2NR^8R^{8'}$, —$NR^8R^{8'}$, —$SO_3H$, =$NOR^8$, —$R^{399}$ and —$R^{400}$ wherein —O—, $R^8$, s, $R^{8'}$, $R^{399}$ add $R^{400}$ are defined as herein;

$R^1$, $R^6$ and $R^7$ in the above are independently selected from the group consisting of (i) hydrogen; (ii) —C($\alpha$NH)NH$_2$; (iii) aryl substituted by $R^{301}$, $R^{302}$ and $R^{303}$ wherein $R^{301}$, $R^{302}$, $R^{303}$ are as defined herein; (iv) heterocyclic substituted by $R^{301}$, $R^{302}$ and $R^{303}$ wherein $R^{301}$, $R^{302}$ and $R^{303}$ are defined as herein; and (v) alkyl having j carbon atoms where j is an integer between 1 and 10, inclusive, substituted with between zero and 5 but no more than j radicals independently selected from the group consisting of —$OR^8$, —$S(O)_sR^8$ where s is an integer between zero and two, inclusive, —$S(O)_2NR^8R^{8'}$, —$NR^8R^{8'}$, —$SO_3H$, =$NOR^8$, —$R^{399}$ and —$R^{400}$ wherein $R^8$, $R^{8'}$, $R^{399}$ and $R^{400}$ are defined as herein;

$R^2$ and $R^3$ are independently selected from the group consisting of (i) hydrogen, (ii) $C_1$-to-$C_8$-loweralkyl, (iii) hydroxy-$C_1$-to-$C_{12}$-alkyl, (iv)—COOH, (v) —COO—($C_1$-to-$C_8$;loweralkyl), (vi) aminoalkyl Of the formula (NR$^{403}$R$^{404}$) $C_1$-to-$C_8$-loweralkyl wherein $R^{403}$ and $R^{404}$ are independently selected from hydrogen, $C_1$-to-$C_8$-loweralkyl, aryl and aryl-$C_1$-to-$C_{12}$-alkyl or, taken together, $R^{403}$ and $R^{404}$ are —(CH$_2$)$_{bb}$— where bb is 2 to 6, (vii) aryl-$C_1$-to-$C_{12}$; alkyl-and (viii) carboxy-$C_1$-to-$C_{12}$-alkyl, or, taken together, $R^2$ and $R^3$ form an oxo group, subject to the proviso that at least one of $R^2$ and $R^3$ must be other than —COOH or —COO—($C_1$-to-$C_8$-loweralkyl);

$R^4$ and $R^5$ are independently selected from the group consisting of hydrogen, hydroxy, amino, mono—($C_1$-to-$C_{12}$-alkyl)amino, $C_1$-to-$C_8$-loweralkyl), hydroxy-$C_1$-to-$C_{12}$-alkyl, —COOH, —COO—($C_1$-to-$C_8$-loweralkyl), aminoalkyl independently as defined above, dialkylamino of the formula —N($C_1$-to-$C_8$-loweralkyl)($C_1$-to-$C_8$-loweralkyl), aryl-$C_1$to-$C_{12}$-alkyl, and carboxy-$C_1$to-$C_{12}$-alkyl, or, taken together, $R^4$ and $R^5$ form an oxo group, subject to the provisos that (i) at least one of $R^4$ and $R^5$ must be other than —COOH or —COO($C_1$-$C_8$-loweralkyl) and (ii) at least one of $R^4$ and $R^5$ must be other than hydroxy, amino, mono—($C_1$-$C_{12}$-alkyllamino or dialkylamino independently as defined above;

n is an integer between zero and five, inclusive;

$R^{399}$ is selected from the group consisting of
(i) hydroxy;
(ii) —C(O)OH;
(iii) —C(O)OR$^8$ wherein $R^8$ is defined as herein;
(iv) —($C_3$-to-$C_7$ cycloalkyl);
(v) oxo;
(vi) thiooxo;
(vii) epoxy;
(viii) halogen;
(ix) —CN;
(x) —$N_3$;
(xi) —$NO_2$;
(xii) $OR_{11'}$ wherein $R^{11'}$ is defined as herein;
(xiii) —$OR_{12'}$ wherein $R_{12'}$ is defined as herein;
(xiv) —$OR_{12''}$ wherein $R^{12'}$ is defined as herein; and
(xv) guanidino substituted by a radical selected from the group consisting of hydrogen, $C_1$-$C_8$-loweralkyl, aryl, $C_1$-$C_{12}$-alkyl-C(O)— or aryl-C(O)—, arylsulfonyl, $C_1$-$C_8$-alkoxycarbonyl, aryl-$C_1$-$C_8$-alkoxycarbonyl, aryloxycarbonyl and $C_1$-$C_{12}$-alkylsulfonyl;

$R^{400}$ is selected from the group consisting of
(i) aryl substituted by $R^{301}$, $R^{302}$ and $R^{303}$;
(ii) —Q-aryl where aryl is substituted by $R^{301}$, $R^{302}$ and $R^{303}$;
(iii) heterocyclic substituted by $R^{301}$, $R^{302}$ and $R^{303}$;
(iv) —Q-heterocyclic where heterocyclic is substituted by $R^{301}$, $R^{302}$ and $R^{303}$;
(v) biaryl substituted by $R^{301}$, $R^{302}$ and $R^{303}$;
(vi) —Q-biaryl where biaryl is substituted by $R^{301}$, $R^{302}$ and $R^{303}$;
(vii) aryl-O-aryl where each aryl group is independently substituted by $R^{301}$, $R^{302}$ and $R^{303}$;
(viii) -aryl-O-heterocyclic where heterocyclic and aryl are independently substituted by $R^{301}$, $R^{302}$ and $R^{303}$;
(ix) -heterocyclic-Q-aryl where heterocyclic and aryl are independently substituted by $R^{301}$, $R^{302}$ and $R^{303}$;
(x) -heterocyclic-aryl where heterocyclic and aryl are independently substituted by $R^{301}$, $R^{302}$ and $R^{303}$; and (xi) -aryl-heterocyclic where heterocyclic and aryl are independently substituted by $R^{301}$, $R^{302}$ and $R^{303}$ wherein at each occurrence, $R^{301}$, $R^{302}$ and $R^{303}$ are defined as herein, where —Q— is a divalent radical selected from the group consisting of (i) —($C_1$-to-$C_6$ alkyl)—,
(ii) —($C_2$-to-$C_6$ alkenyl)—,
(iii) —($C_2$-to-$C_6$ alkynyl)—,
(iv) —$(CH_2)_{m''}O$— where m" is between zero and six, inclusive,
(v) —$O(CH_2)_{m''}$— where m" is defined as above,
(vi) —$N(R^8)C(O)$— wherein $R^8$ is defined as herein,
(vii) —$C(O)N(R^8)$— wherein $R^8$ is defined as herein,
(viii) —$S(O)_s$— wherein s is defined as above,
(ix) —$N(R^8)$— wherein $R^8$ is defined as herein,
(x) —$N(R^8)S(O)_2$- wherein $R^8$ is defined as herein,
(xi) —$S(O)_2N(R^8)$— wherein $R^8$ is defined as herein,
(xii) —C(O)—,
(xiii) —NN—,
(xiv) —CHN—,
(xv) —NCH—,
(xvi) —ONCH—, and
(xvii) —CHNO—;

$R^8$ and $R^{8'}$ are independently selected from the group consisting of
(i) hydrogen;
(ii) aryl substituted by $R^{301}$, $R^{302}$ and $R^{303}$ wherein $R^{301}$, $R^{302}$ and $R^{303}$ are defined as herein;
(iii) heterocyclic substituted by $R^{301}$, $R^{302}$ and $R^{303}$ wherein $R^{301}$, $R^{302}$ and $R^{303}$ are defined as herein,
(iv) —($C_1$-to-$C_6$ alkyl) substituted by $R^{331}$, $R^{332}$ and $R^{333}$ wherein $R^{331}$, $R^{332}$ and $R^{333}$ are defined as herein;
(v) —($C_3$-to-$C_6$ alkenyl) substituted by $R^{331}$, $R^{332}$ and $R^{333}$ wherein $R^{331}$, $R^{332}$, $R^{333}$ are defined as herein; and
(vi) —($C_3$-to-$C_6$ alkynyl) substituted by $R^{331}$, $R^{332}$ and $R^{333}$ wherein $R^{331}$, $R^{332}$ and $R^{333}$ are defined as herein;

$R^{331}$, $R^{332}$ and $R^{333}$ are independently selected from the group consisting of
(A) hydrogen,
(A') halogen,
(B) hydroxy,
(c) mono—($C_1$-to-C 12-alkyl)amino or dialkylamino independently as defined above,
(D) carboxyl,
(E) carboxamido of the formula —$C(C))NH_2$,
(F) thiol,
(G) $C_1$-to-$C_8$-alkylthioether,
(H) $C_1$-to-$C_8$-alkylether,
(I) guanidino,
(J) $C_1$- to-$C_8$-alkoxycarbonyl,
(K) aryl-$C_1$-to-$C_{12}$-alkoxycarbonyl,
(L) $C_1$-to-$C_8$-alkoxy carbonylamino,
(M) acyl independently as defined above,
(N) aryl-$C_1$-to-$C_{12}$-alkoxycarbonylamino,
(O) aryloxycarbonylamino,
(P) acylguanidino wherein acyl is independently as defined above,
(Q) arylsulfonylguanidino,
(R) $C_1$-to-$C_8$-alkoxycarbonylguanidino,
(S) amino,
(T) aryl-$C_1$-to-$C_{12}$-alkoxycarbonylguanidino,
(U) aryloxycarbonylguanidino,
(V) N-alkylcarboxamido of the formula —$C(O)NH(C_1$-to-$C_{12}$-alkyl),
(X) N,N-dialkylcarboxamido Of the formula —$C(O)N(C_1$-to-$C_{12}$-alkyl)($C_1$-to-$C_{12}$-alkyl),
(Y) N-arylcarboxamido,
(Z) N,N-diarylcarboxamido,
(AA) —$OSO_2R^{11}$ where $R_{11}$ is defined as herein,
(BB) oxo,
(CC) epoxy,
(DD) arylether,
(EE) arylthioether,
(FF) aryl-$C_1$-to-$C_{12}$-alkylether,
(GG) aryl-$C_1$-to-$C_{12}$-allylthioether,
(HH) (heterocyclic) ether,
(II) (heterocyclic)thioether,
(JJ) (heterocylic)-$C_1$-to-$C_{12}$-alkylether,
(KK) (heterocyclic)-$C_1$-to-$C_{12}$-alkylthioether,
(LL) aryl,
(MM) heterocyclic,
(NN) —$SO_3H$,
(OO) —$S(O)_2NR^{16'}R_{16''}$ wherein $R^{16'}$, and $R^{16''}$ are defined as herein, and
(PP) —$S(O)_2R_{14'}$ wherein s is defined as above and $R^{14'}$ is defined as herein, where each aryl and heterocyclic moiety is independently substituted by $R^{301}$, $R^{302}$ and $R^{303}$ wherein $R^{301}$, $R^{302}$ and $R^{303}$ are defined as herein, $R_{11}$ is independently selected from the group consisting of $C_1$-to-$C_8$-loweralkyl, aryl-$C_1$-to-$C_{12}$-alkyl substituted by $R^{301}$, $R^{302}$ and $R^{303}$, and aryl substituted by $R^{301}$, $R^{302}$ and $R^{303}$ wherein $R^{301}$, $R^{302}$ and $R^{303}$ are defined as herein, $R_{14'}$ is selected from the group consisting of hydrogen, $C_1$-to-$C_8$-loweralkyl, aryl-$C_1$-to-$C_{12}$-alkyl, $C_3$-to-$C_8$-cycloalkyl and $C_3$-to-$C_8$-cycloalkyl-$C_1$-to$C_8$-alkyl, and $R_{16'}$ and $R_{16''}$ are independently selected from the group consisting of hydrogen, $C_1$-to-$C_8$-loweralkyl, hydroxy-$C_1$-to-$C_8$-loweralkyl, carboxy-$C_1$-to-$C_{12}$-alkyl, thio-$C_1$-to-$C_8$-loweralkyl, thioalkoxy-$C_1$-to-$C_8$-alkyl, guanidino-$C_1$-to-C12-alkyl, aminoalkyl independently as defined aboye and aryl—($C_1$to-$C_{12}$-alkyl;

or, when appended to a nitrogen atom, $R^8$ and $R^{8'}$, taken together with the nitrogen atom to which they are connected, form a 5- to 7-membered heterocyclic ring and $R^{301}$, $R^{302}$ and $R^{303}$ are independently selected from the group consisting of
(i) hydrogen;
(ii) —($C_1$-to-$C_7$ alkyl);
(iii) —($C_2$-to-$C_6$ alkenyl);
(iv) halogen;
(v) —$(CH_2)_mNR^8R^{8'}$, where m is an integer between zero and four, inclusive wherein $R^8$ and $R^{8'}$ are defined as above;
(vi) —CN;
(vii) —CHO;
(viii) mono-, di-, tri-, or perhalogenated $C_1$-$C_{12}$-alkyl;
(ix) —$S(O)_sR^8$ wherein s and $R^8$ are defined as above;
(x) —$C(O)NR^8R^{8'}$ wherein $R^8$ and $R^{8'}$ are defined as above;
(xi) —$(CH_2)_mOR^8$ wherein $R^8$ is defined as above;
(xii) —$CH(OR^{12'})(OR^{12''})$, where $R^{12'}$ and $R^{12''}$ are independently —($C_1$-to-$C_3$ alkyl) or, taken together, form an ethylene or propylene bridge;
(xiii) —$(CH_2)_mOC(O)R^8$ wherein $R^8$ is defined as above;
(xiv) —$(CH_2)_mC(O)OR^8$ wherein $R^8$ is defined as above;
(xv) —$OR_{11'}$, where $R_{11'}$ is selected from the group consisting of (A) —PO(OH)OH (B) —SO₃H, and (C) —C(O)(CH₂)$_m$C(O)O⁻M⁺]-C(O)(CH₂)$_m$C(O)OH;

(xvi) —S(O)₂NR⁸R⁸' wherein R⁸ and R⁸' are defined as above;

(xvii) —NO₂;

(xviii) —N₃; and (xviv) guanidino optionally substituted by a radical selected from the group consisting of C₁-C₈-lower-alkyl, aryl, C₁-C₁₂-alkyl-C(O)— or aryl-C(O)—, arylsulfonyl, C₁-C₈-alkoxycarbonyl, aryl-C₁-C₈-alkoxycarbonyl, aryloxycarbonyl and C₁-C₁₂-alkylsulfonyl, wherein at each occurrence the term aryl is independently selected from phenyl, 1-naphthyl, 2-naphthal, fluorenyl, (1,2)-dihydronaphthyl, indenyl, and indanyl;

wherein at each occurrence the term heterocyclic is independently selected from the group consisting of pyrrolyl, pyrrolidinyl, pyrazolyl, pyrazolinyl, pyrazolidinyl, cytosinyl, thiocytosinyl, imidazolyl, imidazolinyl, imidazolidinyl, pyridyl, piperidinyl, pyrezinyl, piperazinyl, pyrimidinyl, pyridazinyl, xanthenyl, xanthonyl, xanthopterinyl, oxezoyl, oxazolidinyl, thiouracilyl, isoxazolyl, isoxazolidinyl, morpholinyl, indolyl, quinolinyl, uracilyl, urazolyl, uricyl, triazolyl, thiazolidinyl, isothiazolyl, isothiazolidinyl, isoquinolinyl, thyminyl, benzimidazolyl, benzothiazolyl, benzoxazolyl, furyl, thienyl and benzothienyl, subject to the proviso that each of substituents R³⁰¹, R³⁰² and R³⁰³ may comprise no more than twenty non-hydrogen atoms;

or, taken together, any two adjacent groups R³⁰¹, R³⁰² and R³⁰³ and the atoms to which they are attached form a carbocyclic or heterocyclic ring having between five and seven ring atoms.

2. A compound according to claim 1 wherein Z is a radical having the formula

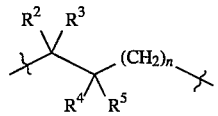

wherein n, R², R³, R⁴ and R⁵ are as defined therein.

3. A compound according to claim 1 wherein n is an integer between zero and five, inclusive.

4. A compound according to claim 1 wherein R¹, R⁶ and R⁷ are independently selected from the group consisting of (i) hydrogen; (ii) —C(=NH)NH₂; (iii) aryl substituted by R³⁰¹, R³⁰² and R³⁰³; and (iv) alkyl having j carbon atoms where j is an integer between 1 and 10, inclusive, substituted with between zero and 5 but no more than j radicals selected from the group consisting of —OR⁸, —S(O)$_s$R⁸ where s is zero through two, —S(O)₂NR⁸R⁸', —NR⁸R⁸', —SO₃H, =NOR⁸, —R³⁹⁹ and —R⁴⁰⁰ wherein s, R⁸, R⁸', R³⁰¹, R³⁰², R³⁰³, R³⁹⁹ and R⁴⁰⁰ are as defined therein. selected from the group consisting of —OR⁸, —S(O)$_s$R⁸, —S(O)₂NR⁸R⁸', —NR⁸R⁸', —SO₃H, 5. A compound according to claim 1 wherein Z is —(C₂-to-C₈ alkylidene)—, optionally substituted with between one and three radicals independently selected from the group consisting of —OR⁸, —S(O)$_s$R⁸, —S(O)₂NR⁸R⁸', —NR⁸R⁸', —SO₃H, =NOR⁸, —R³⁹⁹ and —R⁴⁰⁰ wherein S, R⁸, R⁸', R³⁹⁹ and R⁴⁰⁰ are as defined therein.

6. A compound of the formula:

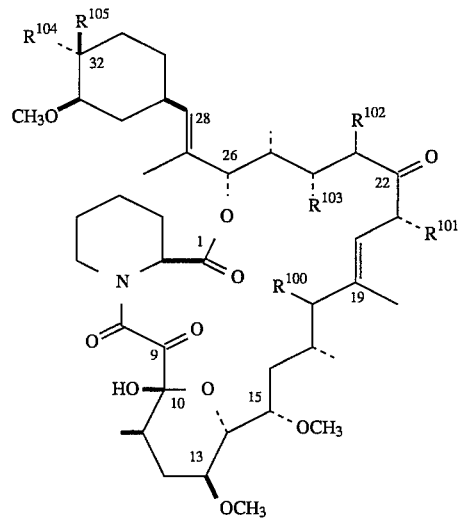

wherein R¹⁰⁵ is a radical having the formula

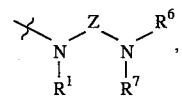

where Z is a divalent radical of the formula

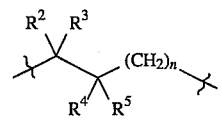

wherein R₁₀₀=H; R₁₀₁=ethyl; R₁₀₂=H; R₁₀₃=OH; R₁₀₄=H; R¹=H; R²=H; R³=H; R⁴=H; R⁵=H; n=1; R⁶=Me; and R⁷=—(CH₂)₃—NH₂; R₁₀₀=H; R₁₀₁=ethyl; R₁₀₂=H; R₁₀₃=OH; R₁₀₄=H; R¹=H; R²=H; R³=H; R⁴=H; R⁵=H; n=1; R⁶=Me; and R⁷=Me; R₁₀₀=H; R₁₀₁=ethyl; R₁₀₂=H; R₁₀₃=OH; R₁₀₄=H; R¹=H; R²=H; R³=H; R⁴=H; R⁵=H; n=21; R⁶=Me; and R⁷=Me; R¹⁰⁰=H; R₁₀₁=ethyl; R₁₀₂=H; R₁₀₃=OH; R₁₀₄=H; R¹=H; R²=H; R³=H; R⁴=H; R⁵=H; n=1; R⁶=Bu; and R⁷=Bu; R₁₀₀=H; R₁₀₁=ethyl; R₁₀₂=H; R₁₀₃=OH; R₁₀₄=H; R¹=H; R²=H; R³= R⁴=H; R⁵=OH; n=1; R⁶=Et; and R⁷=Et; R₁₀₀=H; R₁₀₁=ethyl; R₁₀₂=H; R₁₀₃=OH; R₁₀₄=H; R¹=H; R²=H; R³=H; R⁴=H; R⁵=H; n=1; R⁶=—(CH2)2—OH; and R⁷=(CH₂)₂—OH; R₁₀₀=H; R₁₀₁=ethyl; R₁₀₂=H; R₁₀₃=OH; R₁₀₄=H; R¹ H; R²=H; R³=R⁴=Me; R⁵=Me.; n=1; R⁶=Me; and R⁷=Me; R₁₀₀=H; R₁₀₁=ethyl; R₁₀₂=H; R₁₀₃=OH; R₁₀₄=H; R¹=H; R²=H; R³=H; R⁴=H; R⁵=H; n=0; R⁶=Et; add R⁷=Et; R₁₀₀=H; R₁₀₁=ethyl; R₁₀₂=H; R₁₀₃=OH; R₁₀₄=H; R¹=H; R²=H; R³=H; R⁴=H; R⁵=H; n=0; and R⁶, R⁷ and the nitrogen to which they are attached= NMe₃Cl; R₁₀₀=ethyl; R₁₀₂=H; R₁₀₃=OH; R₁₀₄=H; R¹=H; R²=H; R³=H; R⁴=H; R⁵=H; n=0; R⁶=Me; and R⁷=Me; R₁₀₀=H; R₁₀₁=ethyl; R₁₀₂=H; R₁₀₃=OH; R₁₀₄=H; R¹=H; R²=H; R³=H; R⁴=H; R⁵=H; n=0; R⁶=—(CH2)2—OH; and R⁷=—(CH₂)2—OH; R₁₀₀=H; R₁₀₁=ethyl; R₁₀₂=H; R₁₀₃=OH; R₁₀₄=H; R¹H; R²=H; R³=Me; R⁴=H; R⁵=H; n=0; R⁶=Me; and R⁷=Me; R₁₀₀=H; R₁₀₁=ethyl; R₁₀₂=H; R₁₀₃=OH; R₁₀₄=H; R¹=H; R²=H; R³=H; R⁴=H;

$R^5$=Me; n=0; $R^6$=Me; and $R^7$=Me; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=iPr; and $R^7$=iPr; $R_{100}$=H; $R_{101}$=ethyl; $R_{102}$=H; $R_{103}$=OH; $R_{104}$=H; $R^{1=H;\ R2}$=H; $R^3$=H; $R^4$=H; $R^5$=H; n=0; $R^6$=—(CH$_2$)$_2$—NH$_2$; and $R^7$=C$_{12}$H$_{25}$; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=Et; and $R^7$=—(CH$_2$)$_2$—NEt$_2$; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=Et; and $R^7$=—(CH$_2$)$_2$—OH; $R_{100}$=H; $R_{101}$=ethyl; $R_{102}$=H; $R_{103}$=OH; $R_{104}$=H; $R^1$=H; $R^2$=H; $R^3$=H; $B^4$=H; $R^5$=H; n=0; $R^6$=Me; and $R^7$=Bu; $R_{100}$=H; $R_{101}$=ethyl; $R_{102}$=H; $R_{103}$=OH; $R_{104}$=H; $R_1$=H; $R^2$=H; $R^3$32 CO2H; $R^4$#2 H; $R^5$=H; n=0; $R^6$=Me; and $R^7$=Me; $R_{100}$=H; $R_{101}$=ethyl; $R_{102}$=H; $R_{103}$=OH; $R_{104}$=H; $R^1$=H; $R^2$=CO2H; $R^3$=H; $R^4$=H; $R^5$=H; n=0; $R^6$=Me; and $R^6$=Me; $R_{100}$=H; R101=ethyl; $R_{102}$=H; $R^{103}$32 OH; $R_{104}$=H; $R^1$=Me; $R^2$=H; $R^3$=H; $R^4$=H; $R^5$=H; n=1; $R^6$=Me; and $R^7$=Me; $R_{100}$=H; $R_{101}$=ethyl; $R_{102}$= H; $R_{103}$=OH; $R_{104}$=H; $R^1$=—(CH2)3NMe2; $R^2$H; $R^3$=H; $R^4$=H; $R^5$=H; n=1; $R^6$=Me; and $R^7$=Me; $R_{100}$=H; $R_{101}$=ethyl; $R_{102}$=H; $R_{103}$=OH; $R_{104}$=H; $R^1$=Me; $R^2$=H; $R^3$=H; $R^4$=H; $R^5$=H; n=1; $R^6$=Me; and $R^7$=—(CH$_2$)$_3$NHMe; $R_{100}$=H; $R_{101}$=ethyl; $R_{102}$=H; $R_{103}$=OH; $R_{104}$=H; $R^1$=Et; $R^2$=H; $R^3$=H; $R^4$=H; $R^5$=H; n=1; $R^6$=Et; and $R^7$=—(CH$_2$)$_3$NHEt; $R_{100}$=H; $R_{101}$=ethyl; $R_{102}$=H; $R_{103}$=OH; $R_{104}$=H; $R^{1=Et;}$ $R^2$=H; $R^3$=H; $R^4$=H; $R^5$=H; n=0; $R^6$=Et; and $R^7$=Et; $R_{100}$=H; $R_{101}$=ethyl; $R_{102}$=H; $R_{103}$=OH; $R_{104}$=H; $R^1$=—(CH2)2—OH; $R^2$=H; $R^3$=H; $R^4$=H; $R^5$=H; n=0; $R^6$=Et; and $R^7$=Et; $R_{100}$=H; $R_{101}$=ethyl; $R_{102}$=H; $R_{103}$=OH; $R_{104}$=H; $R^1$=Me; $R^2$=Hl $R^3$=H; $R^4$ and $R^5$ taken together are O; n=0; $R^6$=Me; and $R^7$=CH$_2$—CO$_2$H; $R_{100}$=H; $R_{101}$=ethyl; $R_{102}$=H; $R_{103}$=OH; $R_{104}$=H; $R_1$=Me; Z=—CH2— C($R^{399}$)—; $R^{399}$=oxo; n=0; $R^6$=Me; and $R^Z$=Me; $R_{100}$=H; $R_{101}$=ethyl; $R_{102}$=H; $R_{103}$=OH; $R_{104}$=H; $R^1$=Me; $R^2$=H; $R^3$=H; $R^4$=H; $R^5$=H; n=0; $R^6$=Me; and $R^7$=(CH$_2$)$_2$NHMe; $R_{100}$=H; $R_{101}$=ethyl; $R_{102}$=H; $R_{103}$=OH; $R_{104}$=H; $R^1$—(CH2)2—NEt2; $R^2$=H; $R^3$=H; $R^4$=H; $R^5$=H; n=0; $R^6$=Et; and $R^7$=Et; $R_{100}$=H; $R_{101}$=ethyl; $R_{102}$=H; $R_{103}$=OH; $R_{104}$=H; $R^1$= —(CH2)2— NMe2; $R^2$=H; $R^3$=H; $R^4$= H; $R^5$=H; n=0; $R^6$=Me; and $R^7$=Me; $R_{100}$=H; $R_{101}$=ethyl; $R_{102}$=H; $R_{103}$=OH; $R_{104}$=H; $R^1$=Et; $R^2$=H; $R^3$=H; $R^4$=H; $R^5$=H; n=0; $R^6$=Et; and $R^7$=— (CH$_2$)$_2$NEt(CH$_2$)$_2$NHEt; $R_{100}$=H; R101=ethyl; $R_{102}$=H; $R_{103}$=OH; $R_{104}$=H; $R^1$=H; $R^{2=H;\ R3}$=H; $R^4$=H; $R^5$=H; n=0; $R^6$=H; and $R^7$=—(CH$_2$)$_2$NMe$_2$; $R_{100}$=H; $R_{101}$=ethyl; $R_{102}$=H; $R_{103}$=OH; $R_{104}$=H; $R^1$=—(CH2)2—NH2; $R^2$=H; $R^3$=H; $R^4$= H; R H; n=0; $R^6$=Me; and $R^7$=Me; $R_{100}$=H; $R_{101}$=ethyl; $R_{102}$=H; $R_{103}$=OH; $R_{104}$=H; $R^1$=H; $R^2$=—CO2tBu; $R^3$=H; $R^4$=H; $R^5$=H; n=3; $R^6$=Boc; and $R^7$=H; $R_{101}$=H; $R_{101}$=ethyl; $R_{102}$=H; $R_{103}$=H; $R_{104}$=H; $R^1$=H; $R^2$=—CO2H; $R^3$=H; $R^4$=H; $R^5$=H; n=3; $R^6$=H; and $R^7$=H; $R_{100}$=H; $R_{101}$=ethyl; $R_{102}$=H; $R_{103}$=OH; $R_{104}$=H; $R^1$=H; $R^2$=—CO2H; $R^3$=H; $R^4$=H; $R^5$=H; n=3; $R^6$=H; and $R^7$=—C(=NH)NH$_2$, $R_{100}$=H; $R_{101}$=ethyl; $R_{102}$=H; $R_{103}$=OH; $R_{104}$=H; $R^1$=H; $R^2$32 H; $R^3$= —CO2H; $R^4$=H; $R^5$=H; n=3; $R^6$=H; and $R^7$=H; $R_{100}$=H; $R_{101}$=allyl; $R_{102}$=H; $R_{103}$=OH; $R_{104}$=H; $R^1$=H; $R^2$=H; $R^3$=H; $R^4$=H; $R^5$=H; n=1; $R^6$=Me; and $F^7$=Me; $R_{100}$=H; $R_{101}$=ethyl; $R_{102}$=H; $R_{103}$=OH; $R_{105}$=H; $R^1$=H; $R^2$=H; $R^3$=H; $R^4$=H; $R^5$=H; n=1; $R^6$=Me; and $R^7$=Me; $R_{100}$=H; $R_{101}$=ethyl; $R_{102}$ and $R_{103}$ taken together form a bond; $R_{104}$=H; $R^1$=H; $R^2$=H; $R^3$=H; $R^4$=H; $R^5$=H; n=1; $R^6$=Me; and $R^7$=Me; $R_{100}$=H; $R_{101}$=ethyl; $R_{102}$=H; $R_{103}$=H; $R_{104}$=H; $R^1$=H; $R^2$=H; $R^3$=H; $R^4$=H; $R^5$=H; n=1; $R^6$=Me; and $R^7$=Me; $R_{100}$=H; $R_{101}$=propyl; $R_{102}$=H; $R_{103}$=OH; $R_{104}$=H; $R^1$=H; $R^2$=H; $R^3$=H; $R^4$=H; $R^5$=H; n=1; $R^6$=Me; and $R^7$=Me; $R_{100}$=H; $R_{101}$=methyl; $R_{102}$=H; $R_{103}$=OH; $R_{104}$=H; $R_1$=H; $R^2$=H; $R^3$=H; $R^4$=H; $R^5$=H; n=1; $R^6$= Me; and $R^7$= Me; $R_{100}$=OH; $R_{101}$=ethyl; $R_{102}$=H; $R_{103}$=H; $R_{104}$=H; $R^1$=H; $R^2$=H; $R^3$=H; $R^4$=H; $R^5$=H; n=1; $R^6$=Me; and $R^7$=Me; $R_{100}$=F; $R_{101}$=ethyl; $R_{102}$=H; $R_{103}$=H; $R_{104}$=H; $R^1$=H; $R^2$=H; $R^3$=H; $R^4$=H; $R^5$=H; n=1; $R^5$=Me; and $R^7$=Me; $R_{100}$=OC(O)CH$_3$; $R_{101}$=ethyl; $R_{102}$=H; $R_{103}$=H; $R_{104}$= H; $R^1$=H; $R^2$=H; $R^3$=H; $R^4$=H; $R^5$=H; n=1; $R^6$=Me; and $R^7$=Me; $R_{100}$=H; $R_{101}$=ethyl; $R_{102}$=H; $R_{103}$=OH; $R_{104}$=H; $R^1$=H; $R^2$=H; $R^3$=H; $R^4$=H; $R^5$=H; n=1; $R^6$=Me; and $R^7$=Me; or a pharmaceutically acceptable salt, ester, amide or prodrug thereof.

7. A compound of the formula;

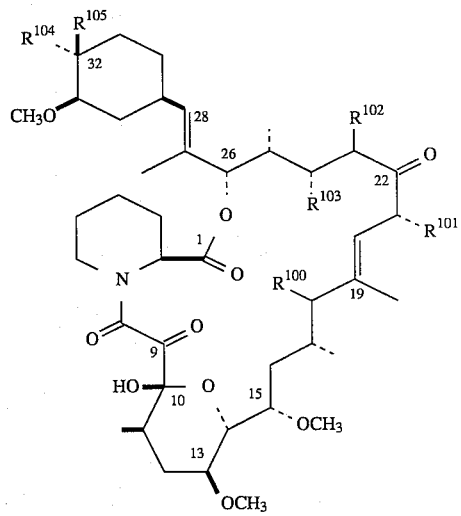

wherein $R_{105}$ is a radical having the formula

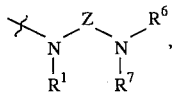

where Z is a divalent radical of the formula

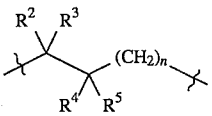

wherein $R_{100}$=H; $R_{101}$=ethyl; $R_{102}$=H; $R_{103}$=OH; $R_{104}$=H; $R^{1=H;\ R2}$=H; $R^3$=H; $R^4$=H; $R^5$=H; n=1; $R^6$=Me; $R^7$=Me; $R_{100}$= H; $R_{101}$=ethyl; $R_{102}$=H; $R_{103}$=OH; $R_{104}$=H; $R^1$=H; $R^2$=H; $R^3$=H; $R^4$=H; $R^5$=H; n=0; $R^6$=Et; $R^7$=Et; $R_{100}$=H; $R_{101}$=ethyl; $R_{102}$=H; $R_{103}$=OH; $R_{104}$=H; $R^1$=Et; $R^2$=H; $R^3$=H; $R^4$=H; $R^5$=H; n=0; $R^6$=Et; $R^7$=Et; or $R_{100}$=H; $R_{101}$=ethyl; $R_{102}$=H; $R_{103}$=OH; $R_{105}$=H; $R^1$=H; $R^2$=H; $R^3$=H; $R^4$=H; $R^5$=H; n=1; $R^6$=Me; $R^7$=Me; or a pharmaceutically acceptable salt, ester, amide or prodrug thereof.

* * * * *

UNITED STATES PATENT AND TRADEMARK OFFICE
CERTIFICATE OF CORRECTION

PATENT NO. : 5,457,194            Page 1 of 6
DATED : October 10, 1995
INVENTOR(S) : Jay R. Luly and Megumi Kawai It is certified that error appears in the above-indentified patent and said Letters Patent is hereby corrected as shown below:

On title page, item [75], "liverty Ville" should be —Libertyville—

In column 36, line 55-58, add Roman numeral "I." to the lower right-hand side under the chemical drawing. Under the chemical drawing, add "or a pharmaceutically acceptable salt, ester, amide, or prodrug thereof wherein the ester" before the text "is selected from".

In column 36, line 64, "Carboxylic" should be "carboxylic".

In column 36, line 66, ".parent" should be "parent", and "druq" should be "drug".

In column 37, line 4, "amines, oxazolidnones" should be "amines, (g) oxazolidinones".

In column 37, line 6, "Z" should be "2".

In column 37, line 8, "-2hydroxymethylpropanol" should be "-2-hydroxymethylpropanol".

In column 37, line 8, "-amino-Z-" should be "-amino-2-".

In column 37, line 12, "$R_{100}$" should be "$R^{100}$".

In column 37, line 23, "methylthiOmethoxyethoxycarbonyl." should be "methylthiomethoxyethoxycarbonyl,".

In column 37, line 49, "-O-" should be "-Q-" and "add" should be "and".

In column 37, line 53, "-C($\alpha$NH)NH$_2$;" should be "-C(=NH)NH$_2$;".

In column 37, line 54, "$R^{302}$, $R^{303}$" should be "$R^{302}$ and $R^{303}$".

UNITED STATES PATENT AND TRADEMARK OFFICE
CERTIFICATE OF CORRECTION

PATENT NO. : 5,457,194          Page 2 of 6
DATED     : October 10, 1995
INVENTOR(S) : Jay R. Luly and Megumi Kawai It is certified that error appears in the above-indentified patent and that said Letters Patent is hereby corrected as shown below:

In column 38, line 1, ";" should be "-".

In column 38, line 1, "Of" should be "of".

In column 38, line 2, "$R^{404}$) $C_1$" should be "$R^{404}$)-$C_1$".

In column 38, line 6, ";" should be "-".

Column 38, line 20, "-COO($C_1$-$C_8$ ...)" should read -- -COO-$C_1$-$C_8$- )

In column 38, line 22, "alkyllamino" should be "alkyl)amino".

In column 38, line 33-34, "(vii) epoxy;" should be one line, not two.

In column 38, line 39, "$OR_{11}$." should be "$OR^{11'}$".

In column 38, line 40, "$OR_{12}$." should be "$OR^{12'}$", and "$R_{12}$." should be "$R^{12'}$".

In column 38, line 41, "$OR_{12}$." should be "$OR^{12'}$", and "$R_{12}$." should be "$R^{12'}$".

In column 38, line 57, "aryl-O-aryl" should be "aryl-Q-aryl".

In column 38, line 59, "-O-" should be "-Q-".

In column 39, line 9, "$m_.$" should be "$m_*$".

In column 39, line 11, "$m_.$" should be "$m_*$".

UNITED STATES PATENT AND TRADEMARK OFFICE
CERTIFICATE OF CORRECTION

PATENT NO. : 5,457,194
DATED : October 10, 1995
INVENTOR(S) : Jay R. Luly and Megumi Kawai It is certified that error appears in the above-indentified patent and that said Letters Patent is hereby corrected as shown below:

In column 39, line 45, "(c)" should be (C)" and "C 12-alkyl)" should be "$C_{12}$-alkyl)".

In column 39, line 48, "-C(C))NH$_2$," should be "-C(O)NH$_2$,"

In column 40, line 1, "Of" should be "of".

In column 40, line 5, "$R_{11}$" should be "$R^{11}$".

In column 40, line 11, "allylthioether," should be "alkylthioether,".

In column 40, line 19, "$R_{16'}$" should be "$R^{16'}$".

In column 40, line 21, "$R_{14'}$" should be "$R^{14'}$".

In column 40, line 26, "$R_{11}$" should be "$R^{11}$".

In column 40, line 31, "$R_{14'}$" should be "$R^{14'}$".

In column 40, line 35, "$R_{16'}$" should be "$R^{16'}$" and "$R_{16'}$" should be "$R^{16'}$".

In column 40, line 40, "aboye" should be "above".

In column 40, line 67, "-OR$_{11'}$" should be "-OR$^{11'}$" and "$R_{11'}$" should be "$R^{11'}$"

In column 41, line 16 and 17, "fiuorenyl" should be "fluorenyl".

In column 41, line 23, "pyrezinyl" should be "pyrazinyl".

UNITED STATES PATENT AND TRADEMARK OFFICE
CERTIFICATE OF CORRECTION

PATENT NO. : 5,457,194          Page 4 of 6
DATED : October 10, 1995
INVENTOR(S) : Jay R. Luly and Megumi Kawai It is certified that error appears in the above-indentified patent and that said Letters Patent is hereby corrected as shown below:

In column 41, line 25, "oxezoyl," should be "oxazoyl,".

In column 41, line 59-61 "selected from the group consisting of $-OR^8$, $-S(O)_sR^8$, $-S(O)_2NR^8R^{8'}$, $-NR^8R^{8'}$, $-SO_3H$," should be deleted.

In column 42, line 45, "n=21" should be "n=2", "$R^{100}$" should be "$R_{100}$".

In column 42, line 49, "$R^3=R^4=H$" should be "$R^3=H$; $R^4=Me$;"

In column 42, line 52, insert "-" so that "$R^7=(CH_2)_2-OH$;" reads "$R^7=-(CH_2)_2-OH$;"

In column 42, line 53, "$R^1$ H;" should be "$R^1=H$".

In column 42, line 53 & 54, "$R^3=R^4=Me$;" should be "$R3=H$; $R4=Me$"

In column 42, line 54, delete the (.) after "$R^5=Me$"

In column 42, line 56, "add" should be "and".

In column 42, line 59, "$R_{100}$=ethyl;" should be "$R_{100}=H$; $R_{101}$=ethyl;"

Column 42, line 64, "$R7=-(CH_2)2-OH$" should be $--R7=-(CH_2)^2-OH--$

In column 42, line 65, "R'H" should be "R'=H".

In column 43, line 4, "$R^1=H$;$R^2=H$;" should be "$R^1=H$; $R^2=H$;"

In column 43, line 6, "$R^7=C_{12}H_{25}$;" should be "$R^7=-C_{12}H_{25}$;"

UNITED STATES PATENT AND TRADEMARK OFFICE
CERTIFICATE OF CORRECTION

PATENT NO. : 5,457,194  
DATED : October 10, 1995  
INVENTOR(S) : Jay R. Luly and Megumi Kawai Page 5 of 6

It is certified that error appears in the above-indentified patent and that said Letters Patent is hereby corrected as shown below:

In column 43, line 12, "B$^4$=H;" should be "R$^4$=H;"

In column 43, line 14, "R$^3$32CO2H;" should be R$^3$=CO2H;" and "R$^4$#2;" should be "R$^4$=H;"

In column 43, line 17, "the second "R$^6$=Me" should be "R$^7$=Me" and "R101=ethyl" should be "R$_{101}$=ethyl".

In column 43, line 18, "R$^{10}$332OH;" should be R$_{103}$=OH;".

In column 43, Line 27, "R$^1$=Et;" should be "R$^1$=Et;".

In column 43, line 28, "$_R$2=H;" should be "R$^2$=H;".

In column 43, line 32, "R$^2$=H1" should be "R$^2$=H;".

In column 43, line 33, "R$^7$=CH$_2$-CO$_2$H;" should be "R$^7$=-CH$_2$-CO$_2$H;".

In column 43, line 36, "R$^Z$" should be "R$^7$".

In column 43, line 38, "R$^7$=(CH$_2$)$_2$NHMe;" should be "R$^7$=-CH$_2$)$_2$NHMe;".

In column 43, line 46, "R101" should be "R$_{101}$".

In column 43, line 47, "R$^2$=H;R$^3$=H;" should be "R$^2$=H; R$^3$=H;".

In column 43, line 50, "RH;" should be "R$^5$=H;".

In column 43, line 53, "R$_{101}$=H;" should be "R$_{100}$=H;".

UNITED STATES PATENT AND TRADEMARK OFFICE
CERTIFICATE OF CORRECTION

PATENT NO. : 5,457,194
DATED : October 10, 1995
INVENTOR(S) : Jay R. Luly and Megumi Kawai It is certified that error appears in the above-indentified patent and that said Letters Patent is hereby corrected as shown below:

In column 43, line 54, "$R_{103}=H$;" should be "$R_{103}=OH$;".

In column 43, line 59, "$R^232H$;" should be "$R^2=H$;".

In column 43, line 62, "$F^7$" should be "$R^7$".

In column 44, line 14, the word "or" is missing before "$R_{100}=H$;".

In column 44, line 57, "$R^1=H;R^2=H$" should be "$R^1=H; R^2=H$;"

In column 44, line 64, "arnide" should be "amide".

Signed and Sealed this

Twenty-third Day of April, 1996

Attest:

BRUCE LEHMAN

Attesting Officer

Commissioner of Patents and Trademarks